(12) United States Patent
Affolter et al.

(10) Patent No.: US 11,701,404 B2
(45) Date of Patent: Jul. 18, 2023

(54) HUMAN MILK FORTIFIER COMPOSITION

(71) Applicant: SOCIETE DES PRODUITS NESTLE S.A., Vevey (CH)

(72) Inventors: Michael Affolter, Savigny (CH); Laurent Ameye, Lausanne (CH); Clara Lucia Garcia-Rodenas, Forel (CH)

(73) Assignee: Societe des Produits Nestle S.A., Vevey (CH)

( * ) Notice: Subject to any disclaimer, the term of this patent is extended or adjusted under 35 U.S.C. 154(b) by 159 days.

(21) Appl. No.: 16/768,776

(22) PCT Filed: Nov. 30, 2018

(86) PCT No.: PCT/EP2018/083141
§ 371 (c)(1),
(2) Date: Jun. 1, 2020

(87) PCT Pub. No.: WO2019/106147
PCT Pub. Date: Jun. 6, 2019

(65) Prior Publication Data
US 2021/0169976 A1    Jun. 10, 2021

(30) Foreign Application Priority Data
Dec. 1, 2017  (EP) .................... 17204996

(51) Int. Cl.
| | | |
|---|---|---|
| *A61K 38/17* | (2006.01) | |
| *A23L 33/19* | (2016.01) | |
| *A23L 33/16* | (2016.01) | |
| *A23L 33/125* | (2016.01) | |
| *A23L 33/00* | (2016.01) | |
| *A23L 33/155* | (2016.01) | |
| *A61P 3/02* | (2006.01) | |
| *A61K 31/07* | (2006.01) | |
| *A61K 31/355* | (2006.01) | |
| *A61K 31/455* | (2006.01) | |
| *A61K 31/702* | (2006.01) | |
| *A61K 31/715* | (2006.01) | |
| *A61K 33/04* | (2006.01) | |
| *A61K 33/30* | (2006.01) | |
| *A61K 33/34* | (2006.01) | |
| *A61K 38/38* | (2006.01) | |

(52) U.S. Cl.
CPC ........ *A61K 38/1709* (2013.01); *A23L 33/125* (2016.08); *A23L 33/155* (2016.08); *A23L 33/16* (2016.08); *A23L 33/19* (2016.08); *A23L 33/40* (2016.08); *A61K 31/07* (2013.01); *A61K 31/355* (2013.01); *A61K 31/455* (2013.01); *A61K 31/702* (2013.01); *A61K 31/715* (2013.01); *A61K 33/04* (2013.01); *A61K 33/30* (2013.01); *A61K 33/34* (2013.01); *A61K 38/38* (2013.01); *A61P 3/02* (2018.01); *A23V 2002/00* (2013.01)

(58) Field of Classification Search
CPC ..................................................... A23L 33/00
See application file for complete search history.

(56) References Cited

U.S. PATENT DOCUMENTS

| | | | |
|---|---|---|---|
| 9,675,649 B2 * | 6/2017 | Bode .................... | A61K 35/742 |
| 2010/0119617 A1 | 5/2010 | O'Connor | |
| 2012/0171166 A1 | 7/2012 | Chow et al. | |
| 2016/0213041 A1 * | 7/2016 | Johns ...................... | A23L 33/19 |
| 2016/0339046 A1 * | 11/2016 | Chow ................ | A61K 31/7004 |
| 2016/0354323 A1 * | 12/2016 | Kuang .................... | A23L 33/40 |

FOREIGN PATENT DOCUMENTS

| | | | | |
|---|---|---|---|---|
| WO | 0060949 | 10/2000 | | |
| WO | WO-2016075243 A1 * | 5/2016 | ........... | C07K 14/245 |
| WO | 2016146789 A1 | 9/2016 | | |
| WO | 2017103019 | 6/2017 | | |

OTHER PUBLICATIONS

Moran et al., "Concentrations and Total Daily Output of Micronutrients in Breast Milk of Mothers Delivering Preterm: A Longitudinal Study" Journal of Pediatric Gastroenteroloty and Nutrition, 1983, vol. 2, pp. 629-634.
Einloft et al., "Supplemented vs. unsupplemented human milk on bone mineralization in very low birth weight preterm infants: a randomized clinical trial" Osteoporosis International, 2015, vol. 26, No. 9, pp. 2265-2271.
Bauer et al. "Longitudinal analysis of macronutrients and minerals in human milk produced by mothers of preterm infants" Clinical Nutrition, 2010, vol. 30, No. 2, pp. 215-220.
Lima Mayara Santa Rosa et al. "Breast milk retinol concentration in mothers of preterm newborns" Early Human Development, 2017, vol. 106, pp. 41-45.
Mehta et al., "Biologically Active Breast Milk Proteins in Association with very Preterm Delivery and Stage of Lactation", Journal of Perinatology, vol. 31, 2011, pp. 58-62, XP037726119.
European Office Action for Appl No. 18 811 541.4-1112 dated Dec. 16, 2022.

\* cited by examiner

*Primary Examiner* — Gina C Justice
(74) *Attorney, Agent, or Firm* — K&L Gates LLP

(57) ABSTRACT

The present invention relates to a preterm human milk fortifier composition, more specifically to a preterm milk fortifier composition providing one or more specific nutrient in amounts that are missing in human milk of women who gave birth to a preterm infant. In particular the present invention relates to a fortifier composition designed for infants as a supplement to preterm human breast milk at the time the infant leaves the hospital (discharge) and after. The invention furthermore relates to the use of said preterm human milk fortifier composition.

7 Claims, 4 Drawing Sheets

Figure 2

| NUTRIENT | Units (g, mg, microg)/L | term (/L) | preterm (/L) | Δ term-preterm (Units/ |
|---|---|---|---|---|
| Proteins | | | | |
| alpha-lactalbumin | g/L | 3.38 | 2.46 | 0.92 g/L |
| caseins | g/L | 7.00 | 5.51 | 1.48 g/L |
| lactoferrin | g/L | 3.28 | 2.56 | 0.73 g/L |
| Minerals | | | | |
| Copper | µg/L | 433.30 | 260.19 | 173.11 µg/L |
| Selenium | µg/L | 15.50 | 12.23 | 3.27 µg/L |
| Zinc | µg/L | 3553.53 | 1257.77 | 2295.76 µg/L |
| Vitamins | | | | |
| alpha-tocopherol | mg/L | 6.90 | 3.61 | 3.30 mg/L |
| gamma-tocopherol | mg/L | 0.42 | 0.38 | 0.04 mg/L |
| total tocopherol | mg/L | 7.33 | 3.99 | 3.34 mg/L |
| Vit A/retinol | mg/L | 1.06 | 0.71 | 0.36 mg/L |
| nicotinic acid | µg/L | 35.31 | 12.28 | 23.03 µg/L |
| HMOs | | | | |
| DFSLTNH | [mg/L] | 194.92 | 77.82 | 117.10 mg/L |
| FSLTNH3 | [mg/L] | 306.32 | 164.52 | 141.79 mg/L |
| GSLT6 | [mg/L] | 51.93 | 20.37 | 31.57 mg/L |
| LnNT | [mg/L] | 209.82 | 140.40 | 69.43 mg/L |
| LNT | [mg/L] | 981.95 | 762.09 | 219.86 mg/L |
| 6'SL | [mg/L] | 414.82 | 150.98 | 263.84 mg/L |
| SLTNTC | [mg/L] | 288.42 | 60.02 | 228.40 mg/L |

Figure 3

| NUTRIENT | Units (g, mg, microg)/L | term (/L) | preterm (/L) | Δ term-preterm (Units/L) |
|---|---|---|---|---|
| Proteins | | | | |
| alpha-lac | g/L | 3.66 | 2.59 | 1.07 g/L |
| caseins | g/L | 7.77 | 5.65 | 2.12 g/L |
| lactoferrin | g/L | 4.02 | 2.73 | 1.29 g/L |
| Minerals | | | | |
| Copper | µg/L | 495.81 | 289.35 | 206.46 µg/L |
| Selenium | µg/L | 17.97 | 12.84 | 5.13 µg/L |
| Zinc | µg/L | 4649.13 | 1485.87 | 3163.26 µg/L |
| Vitamins | | | | |
| alpha-tocopherol | mg/L | 9.77 | 3.57 | 6.20 mg/L |
| gamma-tocopherol | mg/L | 0.47 | 0.36 | 0.11 mg/L |
| total tocopherol | mg/L | 10.24 | 3.93 | 6.31 mg/L |
| Vit A/retinol | mg/L | 1.32 | 0.71 | 0.61 mg/L |
| nicotinic acid | µg/L | 24.67 | 18.36 | 6.31 µg/L |
| HMOs | | | | |
| DFSLTNH | mg/L | 202.13 | 97.77 | 104.36 mg/L |
| FSLTNH3 | mg/L | 310.97 | 193.25 | 117.72 mg/L |
| GSLT6 | mg/L | 78.17 | 22.83 | 55.34 mg/L |
| LnNT | mg/L | 272.59 | 149.06 | 123.53 mg/L |
| LNT | mg/L | 1083.70 | 855.94 | 227.76 mg/L |
| 6-SL | mg/L | 529.97 | 186.08 | 343.89 mg/L |
| SLTNTC | mg/L | 436.90 | 75.60 | 361.30 mg/L |

Figure 4

| NUTRIENT | Units (g, mg, microg)/L | term (/L) | preterm (/L) | Δ term-preterm (Units/L) |
|---|---|---|---|---|
| Amino acids | | | | |
| Glu | g/L | 2.65 | 2.20 | 0.45 g/L |
| Pro | g/L | 1.34 | 1.05 | 0.28 g/L |
| His | g/L | 0.38 | 0.30 | 0.09 g/L |
| Ile | g/L | 0.72 | 0.56 | 0.16 g/L |
| Leu | g/L | 1.57 | 1.22 | 0.34 g/L |
| Lys | g/L | 1.05 | 0.82 | 0.23 g/L |
| Met | g/L | 0.21 | 0.17 | 0.05 g/L |
| Trp | g/L | 0.30 | 0.22 | 0.08 g/L |
| Sum essential AAs (His, Ile, Leu, Lys, Met, Phe, Thr, Trp, Val) | g/L | 6.62 | 4.76 | 1.86 g/L |

US 11,701,404 B2

HUMAN MILK FORTIFIER COMPOSITION

CROSS REFERENCE TO RELATED APPLICATIONS

The present application is a National Stage of International Application No. PCT/EP2018/083141, filed on Nov. 30, 2018, which claims priority to European Patent Application No. 17204996.7, filed on Dec. 1, 2017, the entire contents of which are being incorporated herein by reference.

TECHNICAL FIELD OF THE INVENTION

The present invention relates to a human milk fortifier composition, more specifically to a human milk fortifier composition providing one or more specific nutrients in amounts that are missing in human milk of women who gave birth to a preterm infant. In particular the present invention relates to a fortifier composition designed as a supplement to preterm human breast milk to be used at the time and after the infant leaves the hospital (i.e. post-discharge). The invention furthermore relates to the use of said human milk fortifier composition.

BACKGROUND OF THE INVENTION

Infants are born during different stages of development. For example preterm or premature infants which are infants born before the term of the birth, i.e. before the $37^{th}$ week of gestation, may have a low body weight at birth. Other infants are small for their gestational age, i.e. may for example be born at term, but have a small body weight, such as below 2500 grams. Those infants are typically at risk of growth failure and at increased risk of sub-optimal growth and development and their nutrition is carefully designed and monitored after birth and during their hospitalization at NICU (Neonatal Intensive Care Unit).

Nzegwu et al. ["Post discharge nutrition and the VLBW infants: to supplement or not supplement?", Clin. Perinatol 41 (2014), 463-474] report that nutritional evaluation starts at birth by an anthropometric assessment which provides information on intrauterine growth and continues up to discharge from the hospital to evaluate postnatal growth. Numerous studies underline in fact the importance of early feeding for very low birth weight (VLBW<1500 g) and extremely low birth weight (ELBW<1000) infants for their short and long term growth and development.

Human milk is recognised as the preferred source of enteral nutrition for preterm infants. Anyway, both preterm and term human milk are inadequate to meet the specific nutritional requirements of VLBW infants, so during hospitalization, human milk fortifiers are used to meet the increased nutritional demands of those babies. Feeding human milk during hospitalization has additional and significant advantages for preterm infants, such as decreased risk of NEC (necrotizing enterocolitis) and sepsis, better gastrointestinal tolerance and improved neurologic outcomes.

Nutrition after post-discharge from the hospital is anyway gathering more attention, as it was shown that preterm and especially extremely preterm infants are at a higher risk for growth failure at discharge and that poor growth is associated with impaired neurodevelopment outcomes later on.

The use of human milk fortifiers during NICU hospitalization addresses the disadvantage that human milk doesn't fully address the nutritional needs of preterm infants but it raises questions regarding best choice for post-discharge nutrition for those infants.

Several approaches are available for nutrition during the post-discharge period: infants may, for example, be fed with available post-discharge, standard or preterm formulas, breast-fed or fed with human breast milk fortified with standard, energy dense multinutrient fortifiers, depending on the nutritional status and growth evolution of the infant.

Current evidences about post-discharge nutrition suggest anyway that provision of available post-discharge formulas or standard, energy dense multinutrient fortification of human milk results, in some cases, in minimal improvements in growth and neurodevelopment outcomes. This is possibly due to the fact that preterm infants are able to adjust their volume intake according to the energy content of the feeds; the higher the energy content, the lower the intake (Teller et al, 2016) so that increasing the energy contents of the feeds (for example by using human breast milk fortified with available multinutrient energy dense fortifiers) may ultimately result in an overall insufficient intake of the nutrients needed.

On the other hand, human milk also remains the other nutritional (option for preterm infants at discharge [Nzegwu et al., "Post discharge nutrition and the VLBW infants: to supplement or not supplement?", Clin. Perinatol 41 (2014), 463-474] as well as for those who have reached appropriate weight for post conceptional age at discharge [ESPGHAN, 2006, Journal of Pediatric Gastroenterology and Nutrition, 42: 596-603].

Accordingly, there is still a need to identify ideal feeding solutions adapted to the nutritional needs of infants who were born preterm or VLBW/ELBW, at the time of or after their discharge from hospital.

Thus, an object of the present invention is to provide a human milk fortifier composition to be used at and after discharge from hospital for infants who were born preterm, EVBW or VLBW and which contains correct amounts of specific nutrients (in which respect the human milk of the mothers of such preterm or VLBW infants is deficient).

Additionally, it is an object of the present invention to provide a human milk fortifier composition to be used at discharge from hospital or after in infants who were born preterm, EVBW or VLBW, which contains correct amounts of specific nutrients and which present a high nutrient/energy ratio.

SUMMARY OF THE INVENTION

To address the above-mentioned needs, samples of human milk from mothers of term infants at post menstrual age corresponding to typical discharge window for preterm/VLBW infants were analysed and compared to samples of human milk from mothers of preterm or VLBW infants of the same post menstrual age.

It surprisingly resulted that, at discharge, breast milk received by a preterm baby is poor in alpha-lactalbumin, casein and lactoferrin as compared to milk received by a term baby of the same post-menstrual age. Similarly, at discharge, milk received by a preterm baby is poor in specific micronutrients (Zinc, Selenium, Vit E, Vit A) and certain human milk oligosaccharides (HMOs) as compared to milk received by a term baby of the same post-menstrual age Based on their results, the inventors have designed a fortifier for human milk of mothers who gave birth to preterm or to VLBW or ELBW infants for use at discharge of the infant from the hospital and after. The fortifiers of the present invention have been designed to fill the gap identified and to ensure that infants born preterm, VLBW or ELBW and who at discharge, are fed with their mother's milk, receive nutrition which corresponds to what a term infant of the same post menstrual age would receive through exclusive breast feeding (which remains the gold standard for nutrition and for supporting adequate growth and (neuro) development until 6 months after birth for term babies). At discharge, infants born preterm, ELBW or VLBW are in fact supposed to be on the same growth curve of a term or normal body weight infant of the same postmenstrual age so that their nutritional needs are, at minimum, comparable.

The fortifiers of the present invention additionally provide a high nutrient/energy ratio compared to currently available standard fortifiers. By doing so, the fortifiers of the present invention are expected to have a limited impact on the total milk volume intake of infants and can therefore supplement preterm human breast milk with the essential missing nutrients with a minor impact on total milk volume intake.

Thus, one aspect of the invention relates to a human milk fortifier composition comprising at least one ingredient which delivers minerals, in particular certain amounts of copper, selenium and/or Zinc.

In another aspect, the invention relates to a human milk fortifier composition comprising at least one ingredient which delivers proteins, in particular certain amounts of alpha-lactalbumin, caseins and/or lactoferrin.

In still another aspect, the invention relates to a human milk fortifier composition comprising at least one ingredient which delivers vitamins, in particular certain amounts of total tocopherol (alpha- and/or gamma-tocopherol), retinol and/or nicotinic acid.

In a still further aspect, the invention relates to a human milk fortifier composition comprising at least one ingredient which delivers human milk oligosaccharides, in particular certain amounts of Difucosyllacto-N-Hexaose-a (DFLNHa or DFSLTNH, Monofucosyllacto-N-hexaose-III (MFLNH-III or FSLTNH3), 6'-galactosyllactose (6'GL or GSLT6), Lacto-N-neotetraose (LNnT or LnNT), Lacto-N-tetraose (LNT), 6'-sialyllactose (6'SL), and/or Sialyllactose-N-tetraose-c (LSTc or SLTNTC).

In a still additional aspect, the present invention relates to a human milk fortifier composition comprising at least one ingredient which delivers human milk oligosaccharides, in particular certain amounts of Difucosyllacto-N-Hexaose-a (DFSLTNH, Monofucosyllacto-N-hexaose-III (FSLTNH3), 6'-galactosyllactose (GSLT6), Lacto-N-neotetraose (LnNT), Lacto-N-tetraose (LNT), 6'-sialyllactose (6'SL), and/or Sialyllactose-N-tetraose-c (SLTNTC); at least one ingredient which delivers minerals, in particular certain amounts of copper, selenium and/or Zinc; at least one ingredient which delivers proteins, in particular certain amounts of alpha-lactalbumin, caseins and/or lactoferrin; and at least one ingredient which delivers vitamins, in particular certain amounts of tocopherol (alpha- and/or gamma-tocopherol), retinol and/or nicotinic acid.

In a still another aspect, a human milk fortifier composition is provided comprising at least one ingredient selected in the group consisting of: ingredients providing copper; ingredients providing selenium; ingredients providing zinc; ingredients providing amino acids, for example ingredients providing alpha-lactalbumin, caseins and/or lactoferrin; ingredients providing alpha-tocopherol; ingredients providing gamma-tocopherol; ingredients providing nicotinic acid; ingredients providing retinol; ingredients providing DFSLTHN; ingredients providing FSLTNH3; ingredients providing; 6'-SL; ingredients providing LnNT; ingredients providing LNT; ingredients providing 6'SL; and ingredients providing SLTNTC; Or mixtures thereof.

Yet another aspect of the present invention relates to said human milk fortifier composition for use in fortifying human breast milk, for example human breast milk of mothers who gave birth to preterm, VLBW or ELBW infants at the time of or after discharge from the hospital of the infant who was born preterm, VLBW or ELBW.

Yet another aspect of the present invention relates to the use of said human milk fortifier composition to fortify human breast milk of mothers who gave birth to preterm, VLBW or ELBW infants at discharge from the hospital or after, of an infant who was born preterm, VLBW or ELBW.

In another aspect of the present invention, a human milk fortifier composition is provided for use in prevention and/or treatment of a condition selected in the group consisting of: sub-optimal growth and/or development, stunting of growth, infection, lung disease, developmental delays, blindness and/or bone fractures.

In another aspect of the present invention, use of the human milk fortifier is provided to optimize the growth and development of an infant who was born prematurely, ELBW and/or VLBW.

Still another aspect of the present invention is to provide a package comprising said human milk fortifier composition, wherein the package is a single-dosing device or a multi-dosing device.

In general, the various aspects of the invention may be combined and coupled in any way possible within the scope of the invention. These and other aspects, features and/or advantages of the invention will be apparent from and elucidated with reference to the embodiments described hereinafter.

The present invention will now be described in more details.

BRIEF DESCRIPTION OF THE DRAWINGS

FIG. 2 shows average amounts of certain nutrients measured in breast milk of mothers delivering prematurely when compared with term milk according to corresponding post menstrual age of 38 to 48 weeks.

FIG. 3 shows average amounts of certain nutrients measured in breast milk of mothers delivering prematurely when compared with term milk according to corresponding post menstrual age of 38 to 43 weeks.

FIG. 4 reports results of amino acids' analysis carried out on human breast milk samples collected between weeks 38 and 42 of post menstrual age (samples from 74 term and 29 preterm mothers).

DETAILED DESCRIPTION OF THE INVENTION

Definitions

Figure 1:
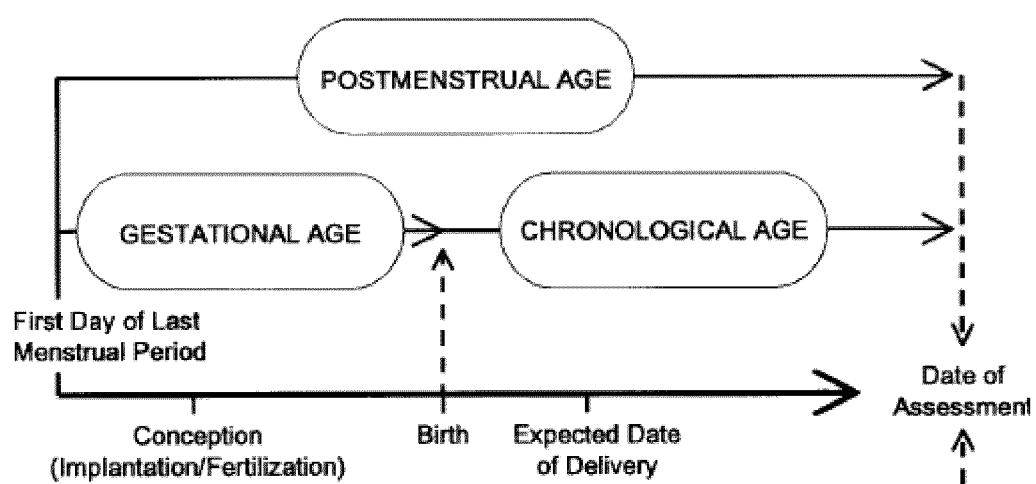
FIG. 1 is a schematic representation of age terminology used during the perinatal period.

Prior to discussing the present invention in further details, the following terms and conventions will first be defined.

Numerical ranges as used herein are intended to include every number and subset of numbers contained within that range, whether specifically disclosed or not.

Further, these numerical ranges should be construed as providing support for a claim directed to any number or subset of numbers in that range. For example, a disclosure of from 1 to 10 should be construed as supporting a range of from 1 to 10 (including 1 and 10), from 2 to 8, from 3 to 7, from 1 to 9, from 3.6 to 4.6, from 3.5 to 9.9, and so forth. All references to singular characteristics or limitations of the present invention shall include the corresponding plural characteristic or limitation, and vice versa, unless otherwise specified or clearly implied to the contrary by the context in which the reference, is made.

The term "and/or" used in the context of the "X and/or Y" should be interpreted as "X", or "Y", or "X and Y".

Unless defined otherwise, all technical and scientific terms used herein have the same meaning as commonly understood by one of ordinary skilled in the art.

Within the context of the present invention, the term "ingredient" or "ingredients" indicates an edible substance or mixture of substances which comprise or is essentially consisting of at least one substance capable of delivering nutrients to the human body.

Within the context of the present invention, the term "ingredient providing nutrient X" or "ingredients providing nutrient X" indicates an edible substance and/or mixture of substances which comprise or is essentially consisting of at least one substance capable of delivering the specified nutrient X to the human body.

Within the context of the present invention, the term "ingredient providing nutrient X in amount Y" or "ingredients providing nutrient X in amount Y" indicates an edible substance and/or mixture of substances which comprise or is essentially consisting of at least one substance capable of delivering the specified nutrient X to the human body in the specified amount Y.

Within the context of the present invention, the term "ingredient providing nutrient X in amount Y/100 mL of human breast milk to be fortified" or 35 "ingredients providing nutrient X in amount Y/100 mL of human breast milk to be fortified" indicates an edible substance and/or mixture of substances which comprise or is essentially consisting of at least one substance capable of delivering the specified nutrient X to the human body in the specified amount Y when a volume of 100 mL of human breast milk is fortified with a composition comprising such ingredient and administered to a subject.

The term "infant" in the context of the present invention identifies a child under the age of 2 years, preferably the infant is a child under the age of 12 months, such as under the age of 9 months, particularly under the age of 6 months.

In the context of the present invention the infant may be any term infant or preterm infant. In an embodiment of the invention, the infant is selected from the group of preterm infants and term infants.

The term "term infant" refers to infants born at term or at a gestational age of 37 weeks or more.

The term "preterm infant" refers to infants who are born at a gestational age of less than 37 weeks.

In the context of the present invention, the term "birth weight" means the first weight of the fetus or newborn obtained after birth.

Within the context of the present invention, the term "low birth weight" means a birth weight of less than 2500 g (up to and including 2499 g).

Within the context of the present invention, the term "very low birth weight" means a birth weight of less than 1500 g (up to and including 1499 g).

Within the context of the present invention, the term "extremely low birth weight" means a birth weight of less than 1000 g (up to and including 999 g).

The term "low body weight infants" refers to infants having a body weight below 2.5 kg at birth.

The term "very low body weight infants" refers to infants having a body weight below 1.5 kg at birth.

The term "extreme low body weight infants" refers to infants having a body weight below 1.0 kg at birth.

The term "small for gestational age infant" refers to infants having a birth weight that is more than 2 standard deviations below the mean reference to a birth weight for gestational growth chart or having a birth weight that is less than the $10^{th}$ percentile of population-based weight data obtained from infants at the same gestational age. The term "small for gestational age infants" includes infants who are small at birth either from a constitutive or genetic origin or, as a consequence of intrauterine growth restriction.

In the context of the present invention, the term "gestational age" indicates a measure of the age of a pregnancy and it is the time elapsed between the first day of the last normal menstrual period and the date of delivery.

Where the date of the last normal menstrual period is not available, gestational age should be based on the best clinical estimate. Gestational age is conventionally expressed as completed weeks. (e.g. events occurring 280 to 286 completed days after the onset of the last normal menstrual period are considered to have occurred at 40 weeks of gestation).

For the purposes of calculation of gestational age from the date of the first day of the last normal menstrual period and the date of delivery, it should be borne in mind that the first day is day zero and not day one; days 0-6 therefore correspond to "completed week zero"; days 7-13 to "completed week one"; and the 40th week of actual gestation is synonymous with "completed week 39".

In the context of the present invention, the term "chronological age" is the time elapsed after birth and may be measured in days, weeks, months and/or years.

In the context of the present invention, the term "post-menstrual age" is the time elapsed between the first day of the last menstrual period and birth (gestational age) plus the time elapsed after birth (chronological age). Post-menstrual age is usually described in number of weeks.

A schematic representation of age terminology used during the perinatal period is provided in FIG. 1.

Within the context of the present invention, the term "perinatal period" indicates a period which commences at 22 completed weeks (154 days) of gestation (the time when birth weight is normally 500 g), and ends seven completed days after birth.

Within the context of the present invention, the term "neonatal period" indicates a period which commences at birth and ends 28 completed days after birth.

Within the context of the present invention the term "at discharge" and/or "at discharge from the hospital" indicates the moment when an infant which was born preterm, ELBW or VLBW is released from the hospital.

In one embodiment, discharge of such infants from the hospital occurs between 36 and 50 weeks, for example between 36 and 48 weeks, of post menstrual age.

The term "infant formula" as used herein refers to a nutritional composition intended for infants and as defined in *Codex Alimentarius*, (Codex STAN 72-1981) and Infant Specialities (incl. Food for Special Medical Purpose) as defined in Codex *Alimentarius*, (Codex STAN 72-1981). It also refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). The infant formulas encompass the starter infant formulas and the follow-up or follow-on formulas. Generally, a starter formula is for infants from birth as breast-milk substitute, and a follow-up or follow-on formula from the 6th month onwards.

The "growing-up milks" (or GUMs) are given from one year onwards. It is generally a milk-based beverage adapted for the specific nutritional needs of young children. They are nutritional compositions used for feeding children from 12 months to 2-3 years old in combination with other foods.

The term "liquid", as used herein, encompass any water- or oil-based composition, for example a fluid, oil, emulsion or a gel.

The term "optimise" as used herein includes improve or enhance.

The composition of the present invention, including the many embodiments described herein, can comprise, consist of, or consist essentially of the essential elements and limitations of the invention described herein, as well as any additional or optional ingredients, components, or limitations described herein or otherwise useful in infant nutritional formula applications.

Fortifier:

Within the context of the present invention, the term "fortifier" refers to a composition which comprises one or more nutrients having a nutritional benefit for infants. In one embodiment, the fortifier according to the present invention comprises at least one nutrient selected in the group consisting of: minerals, vitamins, milk protein and human milk oligosaccharides.

By the term "milk fortifier", it is meant any composition used to fortify or supplement either human breast milk, infant formula, growing-up milk or human breast milk fortified with other nutrients.

By the term "human milk fortifier", it is meant any composition used to fortify or supplement human breast milk, or human breast milk fortified with other nutrients. Accordingly, the human milk fortifier of the present invention can be administered after dissolution in human breast milk, human breast milk fortified with other nutrients or otherwise it can be administered as a stand alone composition.

When administered as a stand-alone composition, the human milk fortifier of the present invention can be also identified as being a "supplement". In one embodiment, the human milk fortifier of the present invention is a supplement.

The "human milk fortifier" according to the present invention is intended to be administered to infants who were born preterm, with very low birth weight (VLBW) or with extremely low birth weight (ELBW).

In one embodiment, the human milk fortifier according to the present invention is intended to be administered to infants who were born preterm, with very low birth weight (VLBW) or with extremely low birth weight (ELBW), starting from the time such infants are discharged from the hospital, typically between 36 and 50 weeks, for example between 38 and 48 weeks, of post-menstrual age.

In one embodiment, the human milk fortifier according to the present invention is intended to be administered to infants who were born preterm, with very low birth weight (VLBW) or with extremely low birth weight (ELBW), starting from the time such infants are discharged from the hospital, typically between 36 and 50 weeks, for example between 38 and 48 weeks, of post-menstrual age, until they reach the post menstrual age of 9 months and/or the body weight of 8 kilograms.

In one embodiment, the human milk fortifier according to the present invention is intended to be administered to infants who were born preterm, with very low birth weight (VLBW) or with extremely low birth weight (ELBW), starting from the time such infants are discharged from the hospital, typically between 38 and 43 weeks, for example between 38 and 42 weeks, of post-menstrual age.

In another embodiment, the human milk fortifier according to the present invention is intended to be administered to infants who were born preterm, with very low birth weight (VLBW) or with extremely low birth weight (ELBW) between 38 and 43 weeks of post-menstrual age.

The milk fortifier may be in the form of powder, tablets, capsules, pastilles or a liquid for example, as long as it is a suitable nutritional composition for the infant. In one embodiment, the human milk fortifier according to the present invention may be in powder of liquid form.

In one embodiment, the human milk fortifier may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The human milk fortifier may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Human milk fortifier compositions having a liquid form presents some particular benefits. For example, liquid formulations might be more convenient if coupled with a packaging that delivers calibrated drops of a certain weight or volume. In some embodiment, liquid human milk fortifier compositions may be packed in single doses in such a way that calibrated drops of a certain weight or volume are delivered while avoiding contamination of the remaining liquid due to manipulation and subsequent uses.

In addition, liquid formulations are easier to mix with the compositions to be fortified, whereas the powder ones can, in some cases, form lumps.

In another embodiment, the milk fortifier according to the present invention can be administered as a stand alone composition.

Further, the supplement may contain an organic or inorganic carrier material suitable for enteral or parenteral administration as well as vitamins, minerals trace elements and other micronutrients in accordance with the recommendations of Government bodies such as the European Commission Directive 2006/141/EC of 22 Dec. 2006 on infant formulae and follow-on formulae.

In one embodiment, the human milk fortifier of the present invention comprises one of the nutrients herebelow described in more detail or combinations thereof.

In another embodiment, the human milk fortifier of the present invention consists of one of the nutrients herebelow described or combinations thereof.

Minerals

In one aspect, the invention relates to a human milk fortifier composition comprising at least one ingredient which delivers minerals, in particular certain amounts of copper, selenium and/or zinc.

Copper

In one embodiment of a human milk fortifier composition is provided which comprises at least one ingredient which delivers copper.

In one embodiment, the fortifier composition of the present invention provides copper in an amount ranging from 5 to 30 μg/100 mL, preferably from 8 to 28 μg/100 mL of human breast milk to be fortified.

In one embodiment, the human milk fortifier composition comprises ingredients which are capable of providing copper in an amount ranging from 5 to 30 μg/g of fortifier. In such embodiment, the recommended fortifier unit dose is of 1 g per 100 mL of human breast milk to be fortified.

In another embodiment, the human milk fortifier composition comprises ingredients which are capable of providing copper in an amount ranging from 1.25 to 7.50 μg/g of fortifier. In such embodiment, the recommended fortifier unit dose is of 4 g per 100 mL of human breast milk to be fortified.

In still another embodiment, the human milk fortifier composition comprises ingredients which are capable of providing copper in an amount ranging from 1 to 6 μg/g of fortifier. In such embodiment, the recommended fortifier unit dose is of 5 g per 100 mL of human breast milk to be fortified.

In one embodiment, the human liquid fortifier of the present invention comprises ingredients providing copper in an amount ranging from 79 to 253 μg, or from 87 to 238 μg or from 107 to 202 μg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing copper are selected in the group consisting of: cupric carbonate, cupric citrate, cupric gluconate, cupric sulphate, cupric lysine complex and mixtures thereof.

As it is evident to the person skilled in the art, different ingredients may provide different amounts of copper in the composition according to the present invention, depending on the nature and amount of the ingredient used. It will be nonetheless routine work to the skilled person to calculate the amount of ingredient needed to provide the claimed amount of copper, based on the specification of the specific ingredient provided by the supplier.

For example, in order to provide copper in the composition in an amount ranging from 5 to 30 μg, copper sulfate may be used in an amount ranging from 13 to 75 μg.

Selenium

In one embodiment of a human milk fortifier composition is provided which comprises at least one ingredient which delivers selenium.

In one embodiment, the fortifier composition of the present invention provides selenium in an amount ranging from 0.1 to 10 μg/100 mL, preferably from 0.3 to 8 μg/100 mL of human breast milk to be fortified.

In one embodiment, the human milk fortifier composition comprises ingredients which are capable of providing selenium in an amount ranging from 0.1 to 10 μg/g of fortifier. In such embodiment, the recommended fortifier unit dose is of 1 g per 100 mL of human breast milk to be fortified.

In another embodiment, the human milk fortifier composition comprises ingredients which are capable of providing selenium in an amount ranging from 0.0025 to 0.25 μg/g of fortifier. In such embodiment, the recommended fortifier unit dose is of 4 g per 100 mL of human breast milk to be fortified.

In still another embodiment, the human milk fortifier composition comprises ingredients which are capable of providing selenium in an amount ranging from 0.002 to 0.2 μg/g of fortifier. In such embodiment, the recommended fortifier unit dose is of 5 g per 100 mL of human breast milk to be fortified.

In one embodiment, the human liquid fortifier of the present invention comprises ingredients providing selenium in an amount ranging from 1 to 7 μg or 2 to 6 μg or 2 to 5 μg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing selenium are selected in the group consisting of: sodium selenite, sodium selenate, sodium hydrogen selenite and mixtures thereof.

As it is evident to the person skilled in the art, different ingredients may provide different amounts of selenium in the composition according to the present invention, depending on the nature and amount of the ingredient used. It will be nonetheless routine work to the skilled person to calculate the amount of ingredient needed to provide the claimed amount of selenium, based on the specification of the specific ingredient provided by the supplier.

For example, in order to provide selenium in the composition in an amount ranging from 0.1 to 10 μg, sodium selenate may be used in an amount ranging from 0.2 to 24 μg.

Zinc

In one embodiment of a human milk fortifier composition is provided which comprises ingredients which delivers zinc.

In one embodiment, the fortifier composition of the present invention provides zinc in an amount ranging from 50 to 550 μg/100 mL, preferably from 100 to 500 μg/100 mL of human breast milk to be fortified.

In one embodiment, the human milk fortifier composition comprises ingredients which are capable of providing zinc in an amount ranging from 50 to 550 μg/g of fortifier. In such embodiment, the recommended fortifier unit dose is of 1 g per 100 mL of human breast milk to be fortified.

In another embodiment, the human milk fortifier composition comprises ingredients which are capable of providing zinc in an amount ranging from 12.5 to 137.5 μg/g of fortifier. In such embodiment, the recommended fortifier unit dose is of 4 g per 100 mL of human breast milk to be fortified.

In still another embodiment, the human milk fortifier composition comprises ingredients which are capable of providing zinc in an amount ranging from 10 to 110 μg/g of fortifier. In such embodiment, the recommended fortifier unit dose is of 5 g per 100 mL of human breast milk to be fortified.

In one embodiment, the liquid human milk fortifier composition comprises ingredients which are capable of providing zinc in an amount ranging from 50 to 550 μg, preferably from 100 to 500 μg.

In one embodiment, the human liquid fortifier of the present invention comprises ingredients providing zinc in an amount ranging from 1220 to 3880 µg or 1340 to 3640 µg or 1640 to 3090 µg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing zinc are selected in the group consisting of: zinc acetate, zinc chloride, zinc citrate, zinc gluconate, zinc lactate, zinc oxide, zinc sulphate, zinc carbonate and mixtures thereof.

As it is evident to the person skilled in the art, different ingredients may provide different amounts of zinc in the composition according to the present invention, depending on the nature and amount of the ingredient used. It will be nonetheless routine work to the skilled person to calculate the amount of ingredient needed to provide the claimed amount of zinc, based on the specification of the specific ingredient provided by the supplier.

For example, in order to provide zinc in the composition in an amount ranging from 50 to 550 µg, zinc sulfate may be used in an amount ranging from 123 to 1358 µg.

Proteins

In another aspect, the invention relates to a human milk fortifier composition comprising at least one ingredient which delivers proteins, in particular alpha-lactalbumin, caseins and/or lactoferrin.

Alpha-Lactalbumin

In one embodiment of a human milk fortifier composition is provided which comprises ingredients which deliver appropriate amounts of alpha-lactalbumin.

In one embodiment, the fortifier composition of the present invention provides alpha-lactalbumin in an amount ranging from 25 to 180 mg/100 mL, preferably from 30 to 150 mg/100 mL of human breast milk to be fortified.

In one embodiment, the human milk fortifier composition comprises ingredients which are capable of providing alpha-lactalbumin in an amount ranging from 25 to 180 mg/g of fortifier. In such embodiment, the recommended fortifier unit dose is of 1 g per 100 mL of human breast milk to be fortified.

In another embodiment, the human milk fortifier composition comprises ingredients which are capable of providing alpha-lactalbumin in an amount ranging from 6.25 to 45 mg/gof fortifier. In such embodiment, the recommended fortifier unit dose is of 4 g per 100 mL of human breast milk to be fortified.

In still another embodiment, the human milk fortifier composition comprises ingredients which are capable of providing alpha-lactalbumin in an amount ranging from 5 to 30 mg/g of fortifier. In such embodiment, the recommended fortifier unit dose is of 5 g per 100 mL of human breast milk to be fortified.

In one embodiment, the liquid human milk fortifier composition comprises ingredients which are capable of providing alpha-lactalbumin in an amount ranging from 25 to 180 mg, preferably from 30 to 150 mg.

In one embodiment, the human liquid fortifier of the present invention comprises ingredients providing alpha-lactalbumin in an amount ranging from 0.4 to 1.31 or 0.45 to 1.23 g or 0.55 to 1.05 g.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing alpha-lactalbumin are selected in the group consisting of: milk (e.g. whole or skimmed milk powder), whey protein (e.g. isolates or concentrates), any other milk powder source and mixtures thereof.

In one additional embodiment, ingredients which are capable of providing alpha-lactalbumin are selected in the group consisting of: skimmed milk (such as for example cow skimmed milk powder), whey protein (such as for example whey protein powder), milk powder (such as for example milk protein isolate) and mixtures thereof.

As it is evident to the person skilled in the art, different ingredients may provide different amounts of alpha-lactalbumin in the composition according to the present invention, depending on the nature and amount of the ingredient used. It will be nonetheless routine work to the skilled person to calculate the amount of ingredient needed to provide the claimed amount of alpha-lactalbumin, based on the specifications of the specific ingredient provided by the supplier.

For example, in order to provide alpha lactalbumin in the composition in an amount ranging from 25 to 180 mg, whey protein powder may be used in an amount ranging from 116 to 835 mg.

Caseins

In one embodiment of a human milk fortifier composition is provided which comprises at least one ingredient which delivers caseins.

In one embodiment, the fortifier composition of the present invention provides caseins in an amount ranging from 01 to 500 mg/100 mL, preferably from 20 to 400 mg/100 mL of human breast milk to be fortified.

In one embodiment, the human milk fortifier composition comprises ingredients which are capable of providing caseins in an amount ranging from 10 to 500 mg/g of fortifier. In such embodiment, the recommended fortifier unit dose is of 1 g per 100 mL of human breast milk to be fortified.

In another embodiment, the human milk fortifier composition comprises ingredients which are capable of providing caseins in an amount ranging from 2.5 to 125 mg/g of fortifier. In such embodiment, the recommended fortifier unit dose is of 4 g per 100 mL of human breast milk to be fortified.

In still another embodiment, the human milk fortifier composition comprises ingredients which are capable of providing caseins in an amount ranging from 2 to 100 mg/g of fortifier. In such embodiment, the recommended fortifier unit dose is of 5 g per 100 mL of human breast milk to be fortified.

In one embodiment, the liquid human milk fortifier composition comprises ingredients which are capable of providing caseins in an amount ranging from 01 to 500 mg, preferably from 20 to 400 mg.

In one embodiment, the human liquid fortifier of the present invention comprises ingredients providing caseins in an amount ranging from 0.82 to 2.60 g or 0.90 to 2.44 g or 1.10 to 2.07 g.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing caseins are selected in the group consisting of:

milk (e.g. whole or skimmed milk powder), whey protein (e.g. isolates or concentrates), any other milk powder source and mixtures thereof.

In one additional embodiment, ingredients which are capable of providing caseins are selected in the group consisting of: fresh whole or skimmed milk, skimmed milk (such as for example cow skimmed milk powder), whole milk (such as for example cow whole milk powder), whey protein (such as for example whey protein powder), milk powder (such as for example milk protein isolate), cream (such as for example pasteurized cream), buttermilk (such as for example buttermilk powder), caseinates (such as for example calcium, potassium and/or sodium caseinate), acid casein and mixtures thereof.

As it is evident to the person skilled in the art, different ingredients may provide different amounts of caseins in the composition according to the present invention, depending on the nature and amount of the ingredient used. It will be nonetheless routine work to the skilled person to calculate the amount of ingredient needed to provide the claimed amount of caseins, based on the specifications of the specific ingredient provided by the supplier.

For example, in order to provide alpha casein in the composition in an amount ranging from 1 to 500 mg, skimmed milk powder may be used in an amount ranging from 4 to 1779 mg.

Lactoferrin

In one embodiment of a human milk fortifier composition is provided which comprises at least one ingredient which deliver lactoferrin.

In one embodiment, the fortifier composition of the present invention provides lactoferrin in an amount ranging from 10 to 500 mg/100 mL, preferably from 20 to 400 mg/100 mL of human breast milk to be fortified.

In one embodiment, the human milk fortifier composition comprises ingredients which are capable of providing lactoferrin in an amount ranging from 10 to 500 mg/g of fortifier. In such embodiment, the recommended fortifier unit dose is of 1 g per 100 mL of human breast milk to be fortified.

In another embodiment, the human milk fortifier composition comprises ingredients which are capable of providing lactoferrin in an amount ranging from 2.5 to 125 mg/g of fortifier. In such embodiment, the recommended fortifier unit dose is of 4 g per 100 mL of human breast milk to be fortified.

In one embodiment, the liquid human milk fortifier composition comprises ingredients which are capable of providing lactoferrin in an amount ranging from 10 to 500 mg, preferably from 20 to 400 mg.

In still another embodiment, the human milk fortifier composition comprises ingredients which are capable of providing lactoferrin in an amount ranging from 2 to 100 mg/g of fortifier. In such embodiment, the recommended fortifier unit dose is of 5 g per 100 mL of human breast milk to be fortified.

In one embodiment, the human liquid fortifier of the present invention comprises ingredients providing lactoferrin in an amount ranging from 0.50 to 1.58 g or 0.55 to 1.58 g or 0.67 to 1.26 g.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

Lactoferrin can be purified from milk or produced recombinantly. Human colostrum has the highest lactoferrin concentration, followed by human milk, then cow milk.

In one embodiment, ingredients which are capable of providing lactoferrrin are commercially available and are selected in the group consisting of: purified or manufactured lactoferrin, whey protein isolate, whey protein concentrate and mixtures thereof.

As it is evident to the person skilled in the art, different ingredients may provide different amounts of caseins in the composition according to the present invention, depending on the nature and amount of the ingredient used. It will be nonetheless routine work to the skilled person to calculate the amount of ingredient needed to provide the claimed amount of caseins, based on the specifications of the specific ingredient provided by the supplier.

For example, in order to provide lactoferrin in the composition in an amount ranging from 10 to 500 mg, a whey protein isolate (for example Vitalarmor® GF-100 Whey Protein Isolate, containing 47% lactoferrin) may be used in an amount ranging from 21 to 1065 mg.

Alternative Sources of Amino Acids

The amounts of alpha-lactalbumin, caseins and/or lactoferrin which the inventors have found to be missing in the analysed preterm milk are ultimately responsible for lower amounts of certain amino acids in such preterm milk as compared to term milk of mother of babies of the same post menstrual age.

Accordingly, as it will be apparent to the skilled person, the human milk fortifier of the present invention could in one embodiment comprise alternative ingredients capable of delivering such amino acids in the amount needed.

Such ingredients could be selected in the group consisting of: milk proteins (for example deriving from cow, goat and/or donkey milk and the like), plant proteins (for example soy), hydrolysates deriving from milk and/or plant proteins, peptides, free amino acids and mixtures thereof.

In one additional embodiment of the present invention, the human milk fortifier may comprise a mixture of ingredients capable of delivering the missing amino acids in the amounts requested; such mixture comprising at least two ingredients selected in the group consisting of: alpha-lactalbumin, caseins, lactoferrin, milk proteins (for example deriving from cow, goat and/or donkey milk and the like), plant proteins (for example soy), hydrolysates deriving from milk and/or plant proteins, peptides, free amino acids and mixtures thereof.

In one embodiment of the present invention, a human milk fortifier composition is provided comprising at least one ingredient which delivers human milk oligosaccharides, in particular certain amounts of Difucosyllacto-N-Hexaose-a (DFSLTNH, Monofucosyllacto-N-hexaose-III (FSLTNH3), 6'-galactosyllactose (GSLT6), Lacto-N-neotetraose (LnNT), Lacto-N-tetraose (LNT), 6'-sialyllactose (6'SL), and/or Sialyllactose-N-tetraose-c (SLTNTC); at least one ingredient which delivers minerals, in particular certain amounts of copper, selenium and/or Zinc; at least one ingredient which delivers amino acids, in particular certain amounts of alpha-lactalbumin, caseins, lactoferrin, milk proteins (for example deriving from cow, goat and/or donkey milk and the like), plant proteins (for example soy), hydrolysates deriving from milk and/or plant proteins, peptides, free amino acids or mixtures thereof; and at least one ingredient which delivers vitamins, in particular certain amounts of tocopherol (alpha- and/or gamma-tocopherol), retinol and/or nicotinic acid.

It is to be understood that all the specific embodiments and combination of nutrients described in the context of the present invention with reference to ingredients providing proteins (alpha-lactalbumin, caseins and/or lactoferrin) would apply mutatis mutandis to the embodiments below described whereby ingredients providing specific amino acids are used as alternative sources of the proteins' building blocks.

In one embodiment of the present invention, a human milk fortifier composition is provided comprising at least one ingredient which delivers human milk oligosaccharides, in particular certain amounts of Difucosyllacto-N-Hexaose-a (DFSLTNH, Monofucosyllacto-N-hexaose-III (FSLTNH3), 6'-galactosyllactose (GSLT6), Lacto-N-neotetraose (LnNT), Lacto-N-tetraose (LNT), 6'-sialyllactose (6'SL), and/or Sialyllactose-N-tetraose-c (SLTNTC); at least one ingredient which delivers minerals, in particular certain amounts of copper, selenium and/or Zinc; at least one ingredient which delivers amino acids, in particular certain amounts of Glu (Glutamic acid), ingredients providing Pro (Proline), ingredients providing His (Histidine), ingredients providing Ile (Isoleucine), ingredients providing Leu (Leucine), ingredients providing Lys (Lysine), ingredients providing Met (Methionine), and ingredients providing Trp (Tryptophan). or mixtures thereof; and at least one ingredient which delivers vitamins, in particular certain amounts of tocopherol (alpha- and/or gamma-tocopherol), retinol and/or nicotinic acid.

In one embodiment of the present invention, a human milk fortifier composition is provided comprising at least one ingredient which delivers human milk oligosaccharides, in particular certain amounts of Difucosyllacto-N-Hexaose-a (DFSLTNH, Monofucosyllacto-N-hexaose-III (FSLTNH3), 6'-galactosyllactose (GSLT6), Lacto-N-neotetraose (LnNT), Lacto-N-tetraose (LNT), 6'-sialyllactose (6'SL), and/or Sialyllactose-N-tetraose-c (SLTNTC); at least one ingredient which delivers minerals, in particular certain amounts of copper, selenium and/or Zinc; at least one ingredient which delivers amino acids, in particular certain amounts of ingredients providing Isoleucine (Ile), Ingredients providing Leucine (Leu), Ingredients providing Methionine (Met), and ingredients providing Proline (Pro) or mixtures thereof; and at least one ingredient which delivers vitamins, in particular certain amounts of tocopherol (alpha- and/or gamma-tocopherol), retinol and/or nicotinic acid.

In one embodiment of the present invention, a human milk fortifier composition is provided comprising at least one ingredient which delivers human milk oligosaccharides, in particular certain amounts of Difucosyllacto-N-Hexaose-a (DFSLTNH, Monofucosyllacto-N-hexaose-III (FSLTNH3), 6'-galactosyllactose (GSLT6), Lacto-N-neotetraose (LnNT), Lacto-N-tetraose (LNT), 6'-sialyllactose (6'SL), and/or Sialyllactose-N-tetraose-c (SLTNTC); at least one ingredient which delivers minerals, in particular certain amounts of copper, selenium and/or Zinc; at least one ingredient which delivers amino acids, in particular certain amounts of essential amino acids, i.e. Histidine (His), Isoleucine (Ile), Leucine (Leu), Lysine (Lys), Methionine (Met), Phenylalanine (Phe), Threonine (Thr), Tryptophan (Trp) and Valine (Val) or mixtures thereof; and at least one ingredient which delivers vitamins, in particular certain amounts of tocopherol (alpha- and/or gamma-tocopherol), retinol and/or nicotinic acid.

Based on the experiments carried out by the present inventors and whose results are reported in FIG. 4, the present invention provides in one embodiment a human milk fortifier composition which comprises at least one ingredient selected in the group consisting of: ingredients providing Isoleucine (Ile), Ingredients providing Leucine (Leu), Ingredients providing Methionine (Met), and ingredients providing Proline (Pro).

In another embodiment, the present invention provides a human milk fortifier composition which comprises at least one ingredient selected in the group consisting of: ingredients providing Glu (Glutamic acid), ingredients providing Pro (Proline), ingredients providing His (Histidine), ingredients providing Ile (Isoleucine), ingredients providing Leu (Leucine), ingredients providing Lys (Lysine), ingredients providing Met (Methionine), and ingredients providing Trp (Tryptophan).

In another embodiment, the present invention provides for a human milk fortifier composition which comprises ingredients providing essential amino acids, i.e. Histidine (His), Isoleucine (Ile), Leucine (Leu), Lysine (Lys), Methionine (Met), Phenylalanine (Phe), Threonine (Thr), Tryptophan (Trp) and Valine (Val).

Glutamic Acid

In one embodiment of a human milk fortifier composition is provided which comprises at least one ingredient which deliver glutamic acid.

In one embodiment, the fortifier composition of the present invention provides glutamic acid in an amount ranging from 5 to 100 mg/100 mL, for example from 10 to 90 mg/100 mL, for example from 30 to 80 mg/100 mL of human breast milk to be fortified.

In one embodiment, the human milk fortifier composition comprises ingredients which are capable of providing glutamic acid in an amount ranging from 5 to 100 mg/g of fortifier. In such embodiment, the recommended fortifier unit dose is of 1 g per 100 mL of human breast milk to be fortified.

In another embodiment, the human milk fortifier composition comprises ingredients which are capable of providing glutamic acid in an amount ranging from 1.25 to 25 mg/g of fortifier. In such embodiment, the recommended fortifier unit dose is of 4 g per 100 mL of human breast milk to be fortified.

In still another embodiment, the human milk fortifier composition comprises ingredients which are capable of providing glutamic acid in an amount ranging from 1 to 20 mg/g of fortifier. In such embodiment, the recommended fortifier unit dose is of 5 g per 100 mL of human breast milk to be fortified.

In one embodiment, the human liquid fortifier of the present invention comprises ingredients providing glutamic acid in an amount ranging from 170 to 560 mg or 190 to 520 mg or 230 to 440 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing glutamic acid are commercially available.

As it is evident to the person skilled in the art, different ingredients may provide different amounts of glutamic acid in the composition according to the present invention, depending on the nature and amount of the ingredient used. It will be nonetheless routine work to the skilled person to calculate the amount of ingredient needed to provide the claimed amount of glutamic acid, based on the specifications of the specific ingredient provided by the supplier.

Proline

In one embodiment of a human milk fortifier composition is provided which comprises at least one ingredient which deliver proline.

In one embodiment, the fortifier composition of the present invention provides proline in an amount ranging from 5 to 60 mg/100 mL, for example from 10 to 50 mg/100 mL, for example from 15 to 40 mg/100 mL of human breast milk to be fortified.

In one embodiment, the human milk fortifier composition comprises ingredients which are capable of providing proline in an amount ranging from 5 to 60 mg/g of fortifier. In such embodiment, the recommended fortifier unit dose is of 1 g per 100 mL of human breast milk to be fortified.

In another embodiment, the human milk fortifier composition comprises ingredients which are capable of providing proline in an amount ranging from 1.25 to 15 mg/g of fortifier. In such embodiment, the recommended fortifier unit dose is of 4 g per 100 mL of human breast milk to be fortified.

In still another embodiment, the human milk fortifier composition comprises ingredients which are capable of providing proline in an amount ranging from 1 to 12 mg/g of fortifier. In such embodiment, the recommended fortifier unit dose is of 5 g per 100 mL of human breast milk to be fortified.

In one embodiment, the human liquid fortifier of the present invention comprises ingredients providing proline in an amount ranging from 105 to 350 mg or 118 to 325 mg or 140 to 275 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing proline are commercially available.

As it is evident to the person skilled in the art, different ingredients may provide different amounts of proline in the composition according to the present invention, depending on the nature and amount of the ingredient used. It will be nonetheless routine work to the skilled person to calculate the amount of ingredient needed to provide the claimed amount of proline, based on the specifications of the specific ingredient provided by the supplier.

Histidine

In one embodiment of a human milk fortifier composition is provided which comprises at least one ingredient which deliver histidine.

In one embodiment, the fortifier composition of the present invention provides histidine in an amount ranging from 1 to 30 mg/100 mL, for example from 2 to 25 mg/100 mL, for example from 3 to 20 mg/100 mL of human breast milk to be fortified.

In one embodiment, the human milk fortifier composition comprises ingredients which are capable of providing histidine in an amount ranging from 1 to 30 mg/g of fortifier. In such embodiment, the recommended fortifier unit dose is of 1 g per 100 mL of human breast milk to be fortified.

In another embodiment, the human milk fortifier composition comprises ingredients which are capable of providing histidine in an amount ranging from 0.25 to 7.5 mg/g of fortifier. In such embodiment, the recommended fortifier unit dose is of 4 g per 100 mL of human breast milk to be fortified.

In still another embodiment, the human milk fortifier composition comprises ingredients which are capable of providing histidine in an amount ranging from 0.2 to 6 mg/g of fortifier. In such embodiment, the recommended fortifier unit dose is of 5 g per 100 mL of human breast milk to be fortified.

30 In one embodiment, the human liquid fortifier of the present invention comprises ingredients providing histidine in an amount ranging from 30 to 120 mg or 35 to 105 mg or 45 to 90 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing histidine are commercially available.

As it is evident to the person skilled in the art, different ingredients may provide different amounts of histidine in the composition according to the present invention, depending on the nature and amount of the ingredient used. It will be nonetheless routine work to the skilled person to calculate the amount of ingredient needed to provide the claimed amount of histidine, based on the specifications of the specific ingredient provided by the supplier.

Isoleucine

In one embodiment of a human milk fortifier composition is provided which comprises at least one ingredient which deliver isoleucine In one embodiment, the fortifier composition of the present invention provides isoleucine in an amount ranging from 1 to 30 mg/100 mL, for example from 2 to 25 mg/100 mL, for example from 3 to 20 mg/100 mL of human breast milk to be fortified.

In one embodiment, the human milk fortifier composition comprises ingredients which are capable of providing isoleucine in an amount ranging from 1 to 30 mg/g of fortifier. In such embodiment, the recommended fortifier unit dose is of 1 g per 100 mL of human breast milk to be fortified.

In another embodiment, the human milk fortifier composition comprises ingredients which are capable of providing isoleucine in an amount ranging from 0.25 to 7.5 mg/g of fortifier. In such embodiment, the recommended fortifier unit dose is of 4 g per 100 mL of human breast milk to be fortified.

In still another embodiment, the human milk fortifier composition comprises ingredients which are capable of providing isoleucine in an amount ranging from 0.2 to 6 mg/g of fortifier. In such embodiment, the recommended fortifier unit dose is of 5 g per 100 mL of human breast milk to be fortified.

In one embodiment, the human liquid fortifier of the present invention comprises ingredients providing isoleucine in an amount ranging from 60 to 200 mg or 65 to 190 mg or 80 to 160 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing isoleucine are commercially available.

As it is evident to the person skilled in the art, different ingredients may provide different amounts of isoleucine in the composition according to the present invention, depending on the nature and amount of the ingredient used. It will be nonetheless routine work to the skilled person to calculate the amount of ingredient needed to provide the claimed amount of isoleucine, based on the specifications of the specific ingredient provided by the supplier.

Leucine

In one embodiment of a human milk fortifier composition is provided which comprises at least one ingredient which deliver leucine.

In one embodiment, the fortifier composition of the present invention provides leucine in an amount ranging from 1 to 100 mg/100 mL, for example from 5 to 80 mg/100 mL, for example from 10 to 70 mg/100 mL of human breast milk to be fortified.

In one embodiment, the human milk fortifier composition comprises ingredients which are capable of providing leucine in an amount ranging from 1 to 100 mg/g of fortifier. In such embodiment, the recommended fortifier unit dose is of 1 g per 100 mL of human breast milk to be fortified.

In another embodiment, the human milk fortifier composition comprises ingredients which are capable of providing leucine in an amount ranging from 0.25 to 25 mg/g of fortifier. In such embodiment, the recommended fortifier unit dose is of 4 g per 100 mL of human breast milk to be fortified.

In still another embodiment, the human milk fortifier composition comprises ingredients which are capable of providing leucine in an amount ranging from 0.2 to 20 mg/g of fortifier. In such embodiment, the recommended fortifier unit dose is of 5 g per 100 mL of human breast milk to be fortified.

In one embodiment, the human liquid fortifier of the present invention comprises ingredients providing leucine in an amount ranging from 130 to 420 mg or 140 to 400 mg or 170 to 335 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing leucine are commercially available.

As it is evident to the person skilled in the art, different ingredients may provide different amounts of leucine in the composition according to the present invention, depending on the nature and amount of the ingredient used. It will be nonetheless routine work to the skilled person to calculate the amount of ingredient needed to provide the claimed amount of leucine, based on the specifications of the specific ingredient provided by the supplier.

Lysine

In one embodiment of a human milk fortifier composition is provided which comprises at least one ingredient which deliver lysine.

In one embodiment, the fortifier composition of the present invention provides 35 lysine in an amount ranging from 1 to 60 mg/100 mL, for example from 5 to 50 mg/100 mL, for example from 10 to 40 mg/100 mL of human breast milk to be fortified.

In one embodiment, the human milk fortifier composition comprises ingredients which are capable of providing lysine in an amount ranging from 5 to 50 mg/g of fortifier. In such embodiment, the recommended fortifier unit dose is of 1 g per 100 mL of human breast milk to be fortified.

In another embodiment, the human milk fortifier composition comprises ingredients which are capable of providing lysine in an amount ranging from 1.25 to 12.5 mg/g of fortifier. In such embodiment, the recommended fortifier unit dose is of 4 g per 100 mL of human breast milk to be fortified.

In still another embodiment, the human milk fortifier composition comprises ingredients which are capable of providing lysine in an amount ranging from 1 to 10 mg/g of fortifier. In such embodiment, the recommended fortifier unit dose is of 5 g per 100 mL of human breast milk to be fortified.

In one embodiment, the human liquid fortifier of the present invention comprises ingredients providing lysine in an amount ranging from 85 to 290 mg or 90 to 270 mg or 115 to 230 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing lysine are commercially available.

As it is evident to the person skilled in the art, different ingredients may provide different amounts of lysine in the composition according to the present invention, depending on the nature and amount of the ingredient used. It will be nonetheless routine work to the skilled person to calculate the amount of ingredient needed to provide the claimed amount of lysine, based on the specifications of the specific ingredient provided by the supplier.

Methionine

In one embodiment of a human milk fortifier composition is provided which comprises at least one ingredient which deliver methionine.

In one embodiment, the fortifier composition of the present invention provides methionine in an amount ranging from 0.1 to 20 mg/100 mL, for example from 0.5 to 15 mg/100 mL, for example from 1 to 10 mg/100 mL of human breast milk to be fortified.

In one embodiment, the human milk fortifier composition comprises ingredients which are capable of providing methionine in an amount ranging from 0.5 to 15 mg/g of fortifier. In such embodiment, the recommended fortifier unit dose is of 1 g per 100 mL of human breast milk to be fortified.

In another embodiment, the human milk fortifier composition comprises ingredients which are capable of providing methionine in an amount ranging from 0.125 to 3.75 mg/g of fortifier. In such embodiment, the recommended fortifier unit dose is of 4 g per 100 mL of human breast milk to be fortified.

In still another embodiment, the human milk fortifier composition comprises ingredients which are capable of providing methionine in an amount ranging from 0.1 to 3 mg/g of fortifier. In such embodiment, the recommended fortifier unit dose is of 5 g per 100 mL of human breast milk to be fortified.

In one embodiment, the human liquid fortifier of the present invention comprises ingredients providing methionine in an amount ranging from 15 to 65 mg or 20 to 60 mg or 25 to 50 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing methionine are commercially available.

As it is evident to the person skilled in the art, different ingredients may provide different amounts of methionine in the composition according to the present invention, depending on the nature and amount of the ingredient used. It will be nonetheless routine work to the skilled person to calculate the amount of ingredient needed to provide the claimed amount of methionine, based on the specifications of the specific ingredient provided by the supplier.

Tryptophan

In one embodiment of a human milk fortifier composition is provided which comprises at least one ingredient which deliver tryptophan.

In one embodiment, the fortifier composition of the present invention provides tryptophan in an amount ranging from 0.5 to 30 mg/100 mL, for example from 1 to 25 mg/100 mL, for example from 2 to 20 mg/100 mL of human breast milk to be fortified.

In one embodiment, the human milk fortifier composition comprises ingredients which are capable of providing tryptophan in an amount ranging from 0.5 to 30 mg/g of fortifier. In such embodiment, the recommended fortifier unit dose is of 1 g per 100 mL of human breast milk to be fortified.

In another embodiment, the human milk fortifier composition comprises ingredients which are capable of providing tryptophan in an amount ranging from 0.125 to 7.5 mg/g of fortifier. In such embodiment, the recommended fortifier unit dose is of 4 g per 100 mL of human breast milk to be fortified.

In still another embodiment, the human milk fortifier composition comprises ingredients which are capable of providing tryptophan in an amount ranging from 0.1 to 6 mg/g of fortifier. In such embodiment, the recommended fortifier unit dose is of 5 g per 100 mL of human breast milk to be fortified.

In one embodiment, the human liquid fortifier of the present invention comprises ingredients providing tryptophan in an amount ranging from 30 to 100 mg or 32 to 95 mg or 40 to 80 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing tryptophan are commercially available.

As it is evident to the person skilled in the art, different ingredients may provide different amounts of tryptophan in the composition according to the present invention, depending on the nature and amount of the ingredient used. It will be nonetheless routine work to the skilled person to calculate the amount of ingredient needed to provide the claimed amount of tryptophan, based on the specifications of the specific ingredient provided by the supplier.

Essential Amino Acids

In one embodiment of a human milk fortifier composition is provided which comprises ingredients which deliver essential aminoacids. In one embodiment, the human milk fortifier composition of the present invention comprises ingredients which deliver Isoleucine (Ile), Leucine (Leu), Methionine (Met).

In one embodiment, the human milk fortifier composition of the present invention comprises ingredients which deliver Histidine (His), Isoleucine (Ile), Leucine (Leu), Lysine (Lys), Methionine (Met), Phenylalanine (Phe), Threonine (Thr), Tryptophan (Trp) and Valine (Val).

In one embodiment, the fortifier composition of the present invention provides essential aminoacids in an amount ranging from 10 to 600 mg/100 mL, for example from 50 to 500 mg/100 mL, for example from 80 to 350 mg/100 mL of human breast milk to be fortified.

In one embodiment, the human milk fortifier composition comprises ingredients which are capable of providing essential aminoacids in an amount ranging from 10 to 600 mg/g of fortifier. In such embodiment, the recommended fortifier unit dose is of 1 g per 100 mL of human breast milk to be fortified.

In another embodiment, the human milk fortifier composition comprises ingredients which are capable of providing essential aminoacids in an amount ranging from 2.5 to 150 mg/g of fortifier. In such embodiment, the recommended fortifier unit dose is of 4 g per 100 mL of human breast milk to be fortified.

In still another embodiment, the human milk fortifier composition comprises ingredients which are capable of providing essential aminoacids in an amount ranging from 2 to 120 mg/g of fortifier. In such embodiment, the recommended fortifier unit dose is of 5 g per 100 mL of human breast milk to be fortified.

In one embodiment, the human liquid fortifier of the present invention comprises ingredients providing essential amino acids in an amount ranging from 700 to 2300 mg or 750 to 2200 mg or 950 to 1850 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing essential amino acids are commercially available.

As it is evident to the person skilled in the art, different ingredients may provide different amounts of essential amino acids in the composition according to the present invention, depending on the nature and amount of the ingredient used. It will be nonetheless routine work to the skilled person to calculate the amount of ingredient needed to provide the claimed amount of essential amino acids, based on the specifications of the specific ingredient provided by the supplier.

Vitamins

In still another aspect, the invention relates to a human milk fortifier composition comprising ingredients which deliver appropriate amounts of vitamins, in particular of tocopherol (alpha- and/or gamma-tocopherol), retinol and/or nicotinic acid.

Total Tocopherol

In one embodiment of a human milk fortifier composition is provided which comprises at least one ingredient which delivers total tocopherol.

Total tocopherol comprises alpha-tocopherol, gamma-tocopherol or mixtures thereof.

In one embodiment, the fortifier composition of the present invention provides total tocopherol in an amount ranging from 5 to 1800 μg/100 mL, preferably from 10 to 1700 μg/100 mL of human breast milk to be fortified.

In one embodiment, the human milk fortifier composition comprises ingredients which are capable of providing total tocopherol in an amount ranging from 5 to 1800 μg/g of fortifier. In such embodiment, the recommended fortifier unit dose is of 1 g per 100 mL of human breast milk to be fortified.

In another embodiment, the human milk fortifier composition comprises ingredients which are capable of providing total tocopherol in an amount ranging from 1.25 to 450 μg/g of fortifier. In such embodiment, the recommended fortifier unit dose is of 4 g per 100 mL of human breast milk to be fortified.

In still another embodiment, the human milk fortifier composition comprises ingredients which are capable of providing total tocopherol in an amount ranging from 1 to 360 µg/g of fortifier. In such embodiment, the recommended fortifier unit dose is of 5 g per 100 mL of human breast milk to be fortified.

In one embodiment, the liquid human milk fortifier composition comprises ingredients which are capable of providing total tocopherol in an amount ranging from 5 to 1800 µg, preferably from 10 to 1700 µg.

In one embodiment, ingredients which are capable of providing total tocopherol are selected in the group consisting of: D-alpha tocopherol, DL-alpha tocopherol, D-alpha tocopheryl acetate, DL-alpha tocopheryl acetate, DL-alpha tocopheryl succinate; DL-alpha tocopheryl polyethylene glycol 1000 succinate and mixtures thereof.

As it is evident to the person skilled in the art, different ingredients may provide different amounts of total tocopherol in the composition according to the present invention, depending on the nature and amount of the ingredient used. It will be nonetheless routine work to the skilled person to calculate the amount of ingredient needed to provide the claimed amount of total tocopherol, based on the specification of the specific ingredient provided by the supplier.

Alpha-Tocopherol

In one embodiment of a human milk fortifier composition is provided which comprises at least one ingredient which delivers alpha-tocopherol.

In one embodiment, the fortifier composition of the present invention provides alpha-tocopherol in an amount ranging from 5 to 1800 µg/100 mL, preferably from 10 to 1700 µg/100 mL of human breast milk to be fortified.

In one embodiment, the human milk fortifier composition comprises ingredients which are capable of providing alpha-tocopherol in an amount ranging from 5 to 1800 µg/g of fortifier. In such embodiment, the recommended fortifier unit dose is of 1 g per 100 mL of human breast milk to be fortified.

In another embodiment, the human milk fortifier composition comprises ingredients which are capable of providing alpha-tocopherol in an amount ranging from 1.25 to 450 µg/g of fortifier. In such embodiment, the recommended fortifier unit dose is of 4 g per 100 mL of human breast milk to be fortified.

In still another embodiment, the human milk fortifier composition comprises ingredients which are capable of providing alpha-tocopherol in an amount ranging from 1 to 360 µg/g of fortifier. In such embodiment, the recommended fortifier unit dose is of 5 g per 100 mL of human breast milk to be fortified.

In one embodiment, the liquid human milk fortifier composition comprises ingredients which are capable of providing alpha-tocopherol in an amount ranging from 5 to 1800 µg, preferably from 10 to 1700 µg.

In one embodiment, the human liquid fortifier of the present invention comprises ingredients providing alpha-tocopherol in an amount ranging from 2.39 to 7.60 mg or 2.64 to 7.13 g or 3.21 to 6.06 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing alpha-tocopherol are selected in the group consisting of: D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate and mixtures thereof.

As it is evident to the person skilled in the art, different ingredients may provide different amounts of alpha-tocopherol in the composition according to the present invention, depending on the nature and amount of the ingredient used. It will be nonetheless routine work to the skilled person to calculate the amount of ingredient needed to provide the claimed amount of alpha-tocopherol, based on the specification of the specific ingredient provided by the supplier.

For example, in order to provide alpha tocopherol in the composition in an amount ranging from 5 to 1800 µg, DL-alpha tocopheryl acetate may be used in an amount ranging from 7 to 2682 µg.

Gamma-Tocopherol

In one embodiment of a human milk fortifier composition is provided which comprises at least one ingredient which delivers gamma-tocopherol.

In one embodiment, the fortifier composition of the present invention provides gamma-tocopherol in an amount ranging from 0.1 to 50 µg/100 mL, preferably from 0.2 to 40 µg/100 mL of human breast milk to be fortified.

In one embodiment, the human milk fortifier composition comprises ingredients which are capable of providing gamma-tocopherol in an amount ranging from 0.1 to 50 µg/g of fortifier. In such embodiment, the recommended fortifier unit dose is of 1 g per 100 mL of human breast milk to be fortified.

In another embodiment, the human milk fortifier composition comprises ingredients which are capable of providing gamma-tocopherol in an amount ranging from 0.025 to 12.5 µg/g of fortifier. In such embodiment, the recommended fortifier unit dose is of 4 g per 100 mL of human breast milk to be fortified.

In still another embodiment, the human milk fortifier composition comprises ingredients which are capable of providing gamma-tocopherol in an amount ranging from 0.02 to 10 µg/g of fortifier. In such embodiment, the recommended fortifier unit dose is of 5 g per 100 mL of human breast milk to be fortified.

In one embodiment, the liquid human milk fortifier composition comprises ingredients which are capable of providing gamma-tocopherol 0.1 to 50 µg, preferably from 0.2 to 40 µg.

In one embodiment, the human liquid fortifier of the present invention comprises ingredients providing gamma-tocopherol in an amount ranging from 0.04 to 0.13 mg or 0.05 to 0.13 mg or 0.06 to 0.11 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

As it is evident to the person skilled in the art, different ingredients may provide different amounts of gamma-tocopherol in the composition according to the present invention, depending on the nature and amount of the ingredient used. It will be nonetheless routine work to the skilled person to calculate the amount of ingredient needed to provide the claimed amount of gamma-tocopherol, based on the specification of the specific ingredient provided by the supplier.

For example, in order to provide gamma tocopherol in the composition in an amount ranging from 0.02 to 10 µg, antioxidants may be used in an amount ranging from 0.071 to 36 µg.

Nicotinic Acid

In one embodiment of a human milk fortifier composition is provided which comprises at least one ingredient which delivers nicotinic acid.

In one embodiment, the fortifier composition of the present invention provides nicotinic acid in an amount ranging from 0.5 to 18 μg/100 mL, preferably from 1 to 15 μg/100 mL of human breast milk to be fortified.

In one embodiment, the human milk fortifier composition comprises ingredients which are capable of providing nicotinic acid in an amount ranging from 0.5 to 18 μg/g of fortifier. In such embodiment, the recommended fortifier unit dose is of 1 g per 100 mL of human breast milk to be fortified.

In another embodiment, the human milk fortifier composition comprises ingredients which are capable of providing nicotinic acid in an amount ranging from 0.125 to 4.5 μg/g of fortifier. In such embodiment, the recommended fortifier unit dose is of 4 g per 100 mL of human breast milk to be fortified.

In still another embodiment, the human milk fortifier composition comprises ingredients which are capable of providing nicotinic acid in an amount ranging from 0.1 to 3.6 μg/g of fortifier. In such embodiment, the recommended fortifier unit dose is of 5 g per 100 mL of human breast milk to be fortified.

In one embodiment, the liquid human milk fortifier composition comprises ingredients which are capable of providing nicotinic acid in an amount ranging from 0.5 to 18 μg, preferably from 1 to 15 μg.

In one embodiment, the human liquid fortifier of the present invention comprises ingredients providing nicotinic acid in an amount ranging from 2.44 to 7.74 μg or 2.68 to 7.26 μg or 3.27 to 6.17 μg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing nicotinic acid are selected in the group consisting of: nicotinic acid, nicotinamide and mixtures thereof.

As it is evident to the person skilled in the art, different ingredients may provide different amounts of nicotinic acid in the composition according to the present invention, depending on the nature and amount of the ingredient used. It will be nonetheless routine work to the skilled person to calculate the amount of ingredient needed to provide the claimed amount of nicotinic acid, based on the specification of the specific ingredient provided by the supplier.

For example, in order to provide nicotinic acid in the composition in an amount ranging from 0.5 to 18 μg, nicotinamide may be used in an amount ranging from 0.5 to 18 μg.

Retinol (Vitamin A)

In one embodiment of a human milk fortifier composition is provided which comprises at least one ingredient which delivers retinol.

In one embodiment, the fortifier composition of the present invention provides retinol in an amount ranging from 1 to 250 μg/100 mL, preferably from 5 to 200 μg/100 mL of human breast milk to be fortified.

In one embodiment, the human milk fortifier composition comprises ingredients which are capable of providing retinol in an amount ranging from 1 to 250 μg/g of fortifier. In such embodiment, the recommended fortifier unit dose is of 1 g per 100 mL of human breast milk to be fortified.

In another embodiment, the human milk fortifier composition comprises ingredients which are capable of providing retinol in an amount ranging from 0.25 to 62.5 μg/g of fortifier. In such embodiment, the recommended fortifier unit dose is of 4 g per 100 mL of human breast milk to be fortified.

In still another embodiment, the human milk fortifier composition comprises ingredients which are capable of providing retinol in an amount ranging from 0.2 to 50 μg/g of fortifier. In such embodiment, the recommended fortifier unit dose is of 5 g per 100 mL of human breast milk to be fortified.

In one embodiment, the liquid human milk fortifier composition comprises ingredients which are capable of providing retinol in an amount ranging from 1 to 250 μg, preferably from 5 to 200 μg.

In one embodiment, the human liquid fortifier of the present invention comprises ingredients providing retinol in an amount ranging from 0.24 to 0.75 mg or 0.26 to 0.70 mg or 0.32 to 0.60 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

In one embodiment, ingredients which are capable of providing retinol are selected in the group consisting of: retinol, retinyl acetate, retinyl palmitate and mixtures thereof.

As it is evident to the person skilled in the art, different ingredients may provide different amounts of retinol in the composition according to the present invention, depending on the nature and amount of the ingredient used. It will be nonetheless routine work to the skilled person to calculate the amount of ingredient needed to provide the claimed amount of retinol, based on the specification of the specific ingredient provided by the supplier.

For example, in order to provide vitamin A (retinol) in the composition in an amount ranging from 1 to 250 μg, retinyl acetate may be used in an amount ranging from 1 to 295 μg.

Human Milk Oligosaccharides

In one embodiment of a human milk fortifier composition is provided which comprises at least one ingredient which delivers appropriate human milk oligosaccharides, in particular Difucosyllacto-N-Hexaose-a (DFSLTNH or DFLNHa, Monofucosyllacto-N-hexaose-III (MFLNH-III or FSLTNH3), 6'-galactosyllactose (6'GL or GSLT6), Lacto-N-neotetraose (LnNT), Lacto-N-tetraose (LNT), 6'-sialyl-lactose (6'SL), or Sialyllactose-N-tetraose-c (sialyllacto-N-tetraose-c or LSTc or SLTNTC) or mixtures thereof.

Throughout the specifications, the following abbreviations may be used to identify the oligosaccharides structures reported in the table below:

Abbreviation(s) Name (Structure)

| | |
|---|---|
| 6'GL or GSLT6 | 6'-galactosyllactose (β-D-Gal-(1 → 6)-β-D-Gal-(1 → 4)-D-Glc) |
| 6'SL | 6'-sialyllactose (α-Neu5Ac-(1 → 6)-β-D-Gal-(1 → 4)-D-Glc) |
| LNT | Lacto-N-tetraose (β-D-Gal-(1 → 3)-β-D-GlcNAc-(1 → 3)-β-D-Gal-(1 → 4)-D-Glc) |

| | -continued |
|---|---|
| LNnT or LnNT | Lacto-N-neotetraose (β-D-Gal-(1 → 4)-β-D-GlcNAc-(1 → 3)-β-D-Gal-(1 → 4)-D-Glc) |
| LSTc or SLTNTC | Sialyllactose-N-tetraose-c or sialyllacto-N-tetraose-c (α-Neu5Ac-(1 → 6)-β-D-Gal-(1 → 4)-β-D-GlcNAc-(1 → 3)-β-D-Gal-(1 → 4)-D-Glc) |
| MFLNH-III or FSLTNH3 | Monofucosyllacto-N-hexaose-III (β-D-Gal(1 → 4)-[α-L-Fuc(1 → 3)-]-β-D-GlcNAc(1 → 6)-[β-D-Gal-(1 → 3)-β-D-GlcNAc-(1 → 3)-]-β-D-Gal-(1 → 4)-D-Glc) |
| DFLNHa or DFSLTNH | Difucosyllacto-N-Hexaose-a (α-L-Fuc-(1 → 2)-β-D-Gal-(1 → 3)-β-D-GlcNAc-(1 → 3)-[β-D-Gal(1 → 4)-β-D-[α-L-Fuc(1 → 3)-]GlcNAc(1 → 6)-β-D-Gal-(1 → 4)-D-Glc) |

Difucosyllacto-N-Hexaose-a (DFSLTNH)

In one embodiment of a human milk fortifier composition is provided which comprises at least one ingredient which delivers DFSLTNH.

In one embodiment, the fortifier composition of the present invention provides DFSLTNH in an amount ranging from 5 to 25 mg/100 mL, preferably from 8 to 15 mg/100 mL of human breast milk to be fortified.

In one embodiment, the human milk fortifier composition comprises ingredients which are capable of providing DFSLTNH in an amount ranging from 5 to 25, for example from 8 to 15) mg/g of fortifier. In such embodiment, the recommended fortifier unit dose is of 1 g per 100 mL of human breast milk to be fortified.

In another embodiment, the human milk fortifier composition comprises ingredients which are capable of providing DFSLTNH in an amount ranging from 1.25 to 6.25, for example 2 to 3.75, mg/g of fortifier. In such embodiment, the recommended fortifier unit dose is of 4 g per 100 mL of human breast milk to be fortified.

In still another embodiment, the human milk fortifier composition comprises ingredients which are capable of providing DFSLTNH in an amount ranging from 1 to 5, for example 1.6 to 3, mg/g of fortifier. In such embodiment, the recommended fortifier unit dose is of 5 g per 100 mL of human breast milk to be fortified.

In one embodiment, the liquid human milk fortifier composition comprises ingredients which are capable of providing DFSLTNH in an amount ranging from 5 to 25 mg, preferably from 8 to 15 mg.

In one embodiment, the human liquid fortifier of the present invention comprises ingredients providing DFSLTHN in an amount ranging from 40 to 128 mg or 44 to 120 mg or 54 to 102 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

Ingredients capable of providing DFSLTHN are commercially available (for example DFSLTHN or DFLNHa: CAS: 64396-27-6 available from Carbosynth with 90% purity).

As it is evident to the person skilled in the art, different ingredients may provide different amounts of DFSLTNH in the composition according to the present invention, depending on the nature and amount of the ingredient used. It will be nonetheless routine work to the skilled person to calculate the amount of ingredient needed to provide the claimed amount of DFSLTNH, based on the specification of the specific ingredient provided by the supplier.

For example, in order to provide DFLNHa in the composition in an amount ranging from 5 to 25 mg, DFLNHa ingredient containing 90% DFLNHa may be used in an amount ranging from 5.56 to 27.8 mg.

MonoFucosyllacto-N-hexaose-III (FSLTNH3 or MFLNH-III)

In one embodiment of a human milk fortifier composition is provided which comprises at least one ingredient which delivers FSLTNH3.

In one embodiment, the fortifier composition of the present invention provides FSLTNH3 in an amount ranging from 0.5 to 35 mg/100 mL, preferably from 5 to 20 mg/100 mL of human breast milk to be fortified.

In one embodiment, the human milk fortifier composition comprises ingredients which are capable of providing FSLTNH3 in an amount ranging from 0.5 to 35, for example 5 to 10, mg/g of fortifier. In such embodiment, the recommended fortifier unit dose is of 1 g per 100 mL of human breast milk to be fortified.

In another embodiment, the human milk fortifier composition comprises ingredients which are capable of providing FSLTNH3 in an amount ranging from 0.125 to 8.75, for example 1.25 to 5, mg/g of fortifier. In such embodiment, the recommended fortifier unit dose is of 4 g per 100 mL of human breast milk to be fortified.

In still another embodiment, the human milk fortifier composition comprises ingredients which are capable of providing FSLTNH3 in an amount ranging from 0.1 to 7, for example 1 to 4) mg/g of fortifier. In such embodiment, the recommended fortifier unit dose is of 5 g per 100 mL of human breast milk to be fortified.

In one embodiment, the liquid human milk fortifier composition comprises ingredients which are capable of providing FSLTNH3 in an amount ranging from 0.5 to 35 mg, preferably from 5 to 20 mg.

In one embodiment, the human liquid fortifier of the present invention comprises ingredients providing FSLTNH3 in an amount ranging from 45 to 145 mg or 50 to 135 mg or 61 to 115 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

Ingredients capable of providing FSLTNH3 are commercially available (for example MFLNH-III available from Dextra).

As it is evident to the person skilled in the art, different ingredients may provide different amounts of FSLTNH3 in the composition according to the present invention, depending on the nature and amount of the ingredient used. It will be nonetheless routine work to the skilled person to calculate the amount of ingredient needed to provide the claimed amount of FSLTNH3, based on the specification of the specific ingredient provided by the supplier.

For example, in order to provide MFLNH-III in the composition in an amount ranging from 0.5 to 35 mg, MFLNH-III ingredient containing 90% MFLNH-III may be used in an amount ranging from 0.56 to 38.9 mg.

6'-galactosyllactose (GSLT6)

In one embodiment of a human milk fortifier composition is provided which comprises at least one ingredient which delivers GSLT6.

In one embodiment, the fortifier composition of the present invention provides GSLT6 in an amount ranging from 0.1 to 10 mg/100 mL, preferably from 1 to 5 mg/100 mL of human breast milk to be fortified.

In one embodiment, the human milk fortifier composition comprises ingredients which are capable of providing GSLT6 in an amount ranging from 0.1 to 10, for example 1 to 5, mg/g of fortifier. In such embodiment, the recommended fortifier unit dose is of 1 g per 100 mL of human breast milk to be fortified.

In another embodiment, the human milk fortifier composition comprises ingredients which are capable of providing GSLT6 in an amount ranging from 0.025 to 2.50, for example 0.25 to 2.5, mg/g of fortifier. In such embodiment, the recommended fortifier unit dose is of 4 g per 100 mL of human breast milk to be fortified.

In still another embodiment, the human milk fortifier composition comprises ingredients which are capable of providing GSLT6 in an amount ranging from 0.02 to 2, for example from 0.2 to 1, mg/g of fortifier. In such embodiment, the recommended fortifier unit dose is of 5 g per 100 mL of human breast milk to be fortified.

In one embodiment, the liquid human milk fortifier composition comprises ingredients which are capable of providing GSLT6 in an amount ranging from 0.1 to 10 mg, preferably from 1 to 5 mg.

In one embodiment, the human liquid fortifier of the present invention comprises ingredients providing GSLT6 in an amount ranging from 21 to 68 mg or 23 to 64 mg or 28 to 54 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

Ingredients capable of providing GSLT6 are commercially available (for example Vivinal GOS or Clasado GOS).

As it is evident to the person skilled in the art, different ingredients may provide different amounts of GSLT6 in the composition according to the present invention, depending on the nature and amount of the ingredient used. It will be nonetheless routine work to the skilled person to calculate the amount of ingredient needed to provide the claimed amount of 6'GL, based on the specification of the specific ingredient provided by the supplier.

For example, in order to provide 6'GL in the composition in an amount ranging from 0.1 to 10 mg, a trans-galactooligosaccharide (GOS) ingredient containing 12 g/100 g of 6'GL may be used in an amount ranging from 0.83 to 83 mg.

Lacto-N-neotetraose (LnNT or LNnT)

In one embodiment of a human milk fortifier composition is provided which comprises at least one ingredient which delivers LnNT.

In one embodiment, the fortifier composition of the present invention provides LnNT in an amount ranging from 0.1 to 25 mg/100 mL, preferably from 1 to 10 mg/100 mL of human breast milk to be fortified.

In one embodiment, the human milk fortifier composition comprises ingredients which are capable of providing LnNT in an amount ranging from 0.1 to 25, for example from 1 to 10, mg/g of fortifier. In such embodiment, the recommended fortifier unit dose is of 1 g per 100 mL of human breast milk to be fortified.

In another embodiment, the human milk fortifier composition comprises ingredients which are capable of providing LnNT in an amount ranging from 0.025 to 6.25, for example from 0.25 to 2.5, mg/g of fortifier. In such embodiment, the recommended fortifier unit dose is of 4 g per 100 mL of human breast milk to be fortified.

In still another embodiment, the human milk fortifier composition comprises ingredients which are capable of providing LnNT in an amount ranging from 0.02 to 5, for example from 0.2 to 22, mg/g of fortifier. In such embodiment, the recommended fortifier unit dose is of 5 g per 100 mL of human breast milk to be fortified.

In one embodiment, the liquid human milk fortifier composition comprises ingredients which are capable of providing LnNT in an amount ranging from 0.1 to 25 mg, preferably from 1 to 10 mg.

In one embodiment, the human liquid fortifier of the present invention comprises ingredients providing LnNT in an amount ranging from 47 to 151 mg or 52 to 142 mg or 64 to 120 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

Ingredients capable of providing LnNT are commercially available.

As it is evident to the person skilled in the art, different ingredients may provide different amounts of LnNT in the composition according to the present invention, depending on the nature and amount of the ingredient used. It will be nonetheless routine work to the skilled person to calculate the amount of ingredient needed to provide the claimed amount of LnNT, based on the specification of the specific ingredient provided by the supplier.

For example, in order to provide LNnT in the composition in an amount ranging from 0.1 to 25 mg, a LNnT ingredient containing 90% LNnT may be used in an amount ranging from 0.11 to 27.8 mg).

Lacto-N-tetraose (LNT)

In one embodiment of a human milk fortifier composition is provided which comprises at least one ingredient which delivers LNT.

In one embodiment, the fortifier composition of the present invention provides LNT in an amount ranging from 0.5 to 55 mg/100 mL, preferably from 5 to 30 mg/100 mL of human breast milk to be fortified.

In one embodiment, the human milk fortifier composition comprises ingredients which are capable of providing LNT in an amount ranging from 0.5 to 55, for example from 5 to 30, mg/g of fortifier. In such embodiment, the recommended fortifier unit dose is of 1 g per 100 mL of human breast milk to be fortified.

In another embodiment, the human milk fortifier composition comprises ingredients which are capable of providing LNT in an amount ranging from 0.125 to 13.75, for example from 1.25 to 7.5, mg/g of fortifier. In such embodiment, the recommended fortifier unit dose is of 4 g per 100 mL of human breast milk to be fortified.

In still another embodiment, the human milk fortifier composition comprises ingredients which are capable of providing LNT in an amount ranging from 0.1 to 11, for example from 1 to 6, mg/g of fortifier. In such embodiment, the recommended fortifier unit dose is of 5 g per 100 mL of human breast milk to be fortified.

In one embodiment, the liquid human milk fortifier composition comprises ingredients which are capable of providing LNT in an amount ranging from 0.5 to 55 mg, preferably from 5 to 30 mg.

In one embodiment, the human liquid fortifier of the present invention comprises ingredients providing LNT in an amount ranging from 87 to 279 mg or 96 to 262 mg or 118 to 222 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

Ingredients capable of providing LNT are commercially available.

As it is evident to the person skilled in the art, different ingredients may provide different amounts of LNT in the composition according to the present invention, depending on the nature and amount of the ingredient used. It will be nonetheless routine work to the skilled person to calculate the amount of ingredient needed to provide the claimed amount of LNT, based on the specification of the specific ingredient provided by the supplier.

For example, in order to provide Lacto-N-tetraose (LNT) in the composition in an amount ranging from 0.5 to 55 mg, a Lacto-N-tetraose ingredient containing 95% LNT may be used in an amount ranging from 0.53 to 57.9 mg.

6'-sialyllactose (6'SL)

In one embodiment of a human milk fortifier composition is provided which comprises at least one ingredient which delivers 6'SL.

In one embodiment, the fortifier composition of the present invention provides 6'SL in an amount ranging from 5 to 355 mg/100 mL, preferably from 15 to 35 mg/100 mL of human breast milk to be fortified.

In one embodiment, the human milk fortifier composition comprises ingredients which are capable of providing 6'SL in an amount ranging from 5 to 55, for example from 15 to 35, mg/g of fortifier. In such embodiment, the recommended fortifier unit dose is of 1 g per 100 mL of human breast milk to be fortified.

In another embodiment, the human milk fortifier composition comprises ingredients which are capable of providing 6'SL in an amount ranging from 1.25 to 13.75, for example from 3.75 to 8.75, mg/g of fortifier. In such embodiment, the recommended fortifier unit dose is of 4 g per 100 mL of human breast milk to be fortified.

In still another embodiment, the human milk fortifier composition comprises ingredients which are capable of providing 6'SL in an amount ranging from 1 to 11, for example from 3 to 7, mg/g of fortifier. In such embodiment, the recommended fortifier unit dose is of 5 g per 100 mL of human breast milk to be fortified.

In one embodiment, the liquid human milk fortifier composition comprises ingredients which are capable of providing 6'SL in an amount ranging from 5 to 355 mg, preferably from 15 to 35 mg.

In one embodiment, the human liquid fortifier of the present invention comprises ingredients providing 6'SL in an amount ranging from 132 to 421 mg or from 146 to 395 mg or 178 to 336 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

Ingredients capable of providing 6'-SL are commercially available.

As it is evident to the person skilled in the art, different ingredients may provide different amounts of 6'SL in the composition according to the present invention, depending on the nature and amount of the ingredient used. It will be nonetheless routine work to the skilled person to calculate the amount of ingredient needed to provide the claimed amount of 6'SL, based on the specification of the specific ingredient provided by the supplier.

For example, in order to provide 6'SL in the composition in an amount ranging from 5 to 355 mg, 6'-O-Sialyllactose sodium salt may be used in an amount ranging from 5.2 to 367.3 mg Sialyllactose-N-tetraose-c (SLTNTC or LSTc)

In one embodiment of a human milk fortifier composition is provided which comprises at least one ingredient which delivers SLTNTC.

In one embodiment, the fortifier composition of the present invention provides SLTNTC in an amount ranging from 1 to 60 mg/100 mL, preferably from 1 to 30 mg/100 mL of human breast milk to be fortified.

In one embodiment, the human milk fortifier composition comprises ingredients which are capable of providing SLTNTC in an amount ranging from 1 to 60, for example from 1 to 30, mg/g of fortifier. In such embodiment, the recommended fortifier unit dose is of 1 g per 100 mL of human breast milk to be fortified.

In another embodiment, the human milk fortifier composition comprises ingredients which are capable of providing SLTNTC in an amount ranging from 0.25 to 15, for example from 2.5 to 7.5, mg/g of fortifier. In such embodiment, the recommended fortifier unit dose is of 4 g per 100 mL of human breast milk to be fortified.

In still another embodiment, the human milk fortifier composition comprises ingredients which are capable of providing SLTNTC in an amount ranging from 0.2 to 12, for example from 2 to 6, mg/g of fortifier. In such embodiment, the recommended fortifier unit dose is of 5 g per 100 mL of human breast milk to be fortified.

In one embodiment, the liquid human milk fortifier composition comprises ingredients which are capable of providing SLTNTC in an amount ranging from 1 to 60 mg, preferably from 1 to 30 mg.

In one embodiment, the human liquid fortifier of the present invention comprises ingredients providing SLTNTC in an amount ranging from 139 to 443 mg or 153 to 415 mg or 187 to 353 mg.

In such embodiment, the human milk liquid fortifier may be administered as a stand alone composition and the nutrient's amount split into 1, 2, 3, 4, 5 or 6 daily single doses. For example, the nutrient's amount may be split into 1, 3 or 6 daily single doses.

Ingredients capable of providing SLTNTC are commercially available.

As it is evident to the person skilled in the art, different ingredients may provide different amounts of SLTNTC in the composition according to the present invention, depending on the nature and amount of the ingredient used. It will be nonetheless routine work to the skilled person to calculate the amount of ingredient needed to provide the claimed amount of SLTNTC, based on the specification of the specific ingredient provided by the supplier.

For example, in order to provide LSTc in the composition in an amount ranging from 1 to 60 mg, LSTc sodium salt may be used in an amount ranging from 1.02 to 61.3 mg Specific Embodiments In one embodiment, the present invention provides for a human milk fortifier composition comprising at least one ingredient selected in the group consisting of:
- ingredients providing copper, for example cupric carbonate, cupric citrate, cupric gluconate, cupric sulphate, cupric lysine complex or mixtures thereof;
- ingredients providing selenium, for example sodium selenite, sodium selenate, sodium hydrogen selenite or mixtures thereof;
- ingredients providing zinc, for example zinc acetate, zinc chloride, zinc citrate, zinc gluconate, zinc lactate, zinc oxide, zinc sulphate, zinc carbonate or mixtures thereof;
- ingredients providing alpha-lactalbumin, for example milk (e.g. whole or skimmed milk powder), whey protein (e.g. isolates or concentrates), milk powder sources or mixtures thereof;
- ingredients providing casein, for example milk (e.g. whole or skimmed milk powder), whey protein (e.g. isolates or concentrates), milk powder sources or mixtures thereof;
- ingredients providing lactoferrin, for example purified or manufactured lactoferrin, whey protein isolate, whey protein concentrate or mixtures thereof;
- ingredients providing alpha-tocopherol, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;
- ingredients providing gamma-tocopherol;
- ingredients providing nicotinic acid, for example nicotinic acid, nicotinamide or mixtures thereof;
- ingredients providing retinol, for example retinol, retinyl acetate, retinyl palmitate or mixtures thereof;
- ingredients providing DFSLTHN, for example Difucosyllacto-N-Hexaose-a;
- ingredients providing FSLTNH3, for example Monofucosyllacto-N-hexaose-III;
- ingredients providing GSLT6, for example 6'-galactosyllactose;
- ingredients providing LnNT, for example Lacto-N-neotetraose;
- ingredients providing LNT, for example Lacto-N-tetraose;
- ingredients providing 6'SL, for example 6'-sialyllactose or 6'-sialyllactose sodium salt; and
- ingredients providing SLTNTC, for example Sialyllactose-N-tetraose-c; Or mixtures thereof.

In another embodiment, the present invention provides for a human milk fortifier comprising at least one ingredient selected in the group consisting of:
- ingredients providing copper in an amount ranging from 5 to 30 µg/g or 1.5 to 7.50 µg/g or 1 to 6 µg/g of fortifier, for example cupric carbonate, cupric citrate, cupric gluconate, cupric sulphate, cupric lysine complex or mixtures thereof;
- ingredients providing selenium in an amount ranging from 0.1 to 10 µg/g or 0.0025 to 25 µg/g or 0.002 to 0.2 µg/g of fortifier, for example sodium selenite, sodium selenate, sodium hydrogen selenite or mixtures thereof;
- ingredients providing zinc in an amount ranging from 50 to 550 µg/g or 12.5 to 137.5 µg/g or 10 to 110 µg/g of fortifier, for example zinc acetate, zinc chloride, zinc citrate, zinc gluconate, zinc lactate, zinc oxide, zinc sulphate, zinc carbonate or mixtures thereof;
- ingredients providing alpha-lactalbumin in an amount ranging from 25 to 180 mg/g or 6.25 to 45 mg/g or 5 to 30 mg/g of fortifier, for example milk (e.g. whole or skimmed milk powder), whey protein (e.g. isolates or concentrates), milk powder sources or mixtures thereof;
- ingredients providing caseins in an amount ranging from 10 to 500 mg/g or 2.5 to 125 mg/g or 2 to 100 mg/g of fortifier, for example milk (e.g. whole or skimmed milk powder), whey protein (e.g. isolates or concentrates), milk powder sources or mixtures thereof;
- ingredients providing lactoferrin in an amount ranging from 10 to 500 mg/g or 2.5 to 125 mg/g or 2 to 100 mg/g of fortifier, for example purified or manufactured lactoferrin, whey protein isolate, whey protein concentrate or mixtures thereof;
- ingredients providing alpha-tocopherol in an amount ranging from 5 to 1800 µg/g or 1.25 to 450 µg/g or 1 to 360 µg/g of fortifier, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;
- ingredients providing gamma-tocopherol in an amount ranging from 0.1 to 50 µg/g or 0.025 to 12.5 µg/g or 0.02 to 10 µg/g of fortifier;
- ingredients providing nicotinic acid in an amount ranging from 0.5 to 18 µg/g or 0.25 to 4.25 µg/g or 0.1 to 3.6 µg/g of fortifier, for example nicotinic acid, nicotinamide or mixtures thereof;
- ingredients providing retinol in an amount ranging from 1 to 250 µg/g or 0.25 to 62.5 µg/g or 0.2 to 50 µg/g of fortifier, for example retinol, retinyl acetate, retinyl palmitate or mixtures thereof;
- ingredients providing DFSLTHN in an amount ranging from 5 to 25 mg/g or 1.25 to 6.25 mg/g or 1 to 5 mg/g of fortifier, for example Difucosyllacto-N-Hexaose-a;
- ingredients providing FSLTNH3 in an amount ranging from 0.5 to 35 mg/g or 0.125 to 8.75 mg/g or 0.1 to 7 mg/g of fortifier, for example Monofucosyllacto-N-hexaose-III;
- ingredients providing GSLT6 in an amount ranging from 0.1 to 10 mg/g or 0.025 to 2.5 mg/g or 0.02 to 2 mg/g of fortifier, for example 6'-galactosyllactose;
- ingredients providing LnNT in an amount ranging from 0.1 to 25 mg/g or 0.025 to 6.25 mg/g or 0.02 to 5 mg/g of fortifier, for example Lacto-N-neotetraose;
- ingredients providing LNT in an amount ranging from 0.5 to 55 mg/g or 0.125 to 13.75 mg/g or 0.1 to 11 mg/g of fortifier, for example Lacto-N-tetraose;
- ingredients providing 6'SL in an amount ranging from 5 to 55 mg/g or 1.25 to 13.75 mg/g or 1 to 11 mg/g of fortifier, for example 6'-sialyllactose or 6'-sialyllactose sodium salt; and
- ingredients providing SLTNTC in an amount ranging from 1 to 60 mg/g or 0.25 to 15 mg/g or 0.2 to 12 mg/g of fortifier, for example Sialyllactose-N-tetraose-c; Or mixtures thereof.

In one embodiment, a human milk fortifier composition is provided comprising:
- ingredients providing zinc in an amount ranging from 50 to 550 µg/g or 12.5 to 137.5 µg/g or 10 to 110 µg/g of fortifier, for example zinc acetate, zinc chloride, zinc citrate, zinc gluconate, zinc lactate, zinc oxide, zinc sulphate, zinc carbonate or mixtures thereof;

ingredients providing alpha-lactalbumin in an amount ranging from 25 to 180 mg/g or 6.25 to 45 mg/g or 5 to 30 mg/g of fortifier, for example milk (e.g. whole or skimmed milk powder), whey protein (e.g. isolates or concentrates), milk powder sources or mixtures thereof;

ingredients providing caseins in an amount ranging from 10 to 500 mg/g or 2.5 to 125 mg/g or 2 to 100 mg/g of fortifier, for example milk (e.g. whole or skimmed milk powder), whey protein (e.g. isolates or concentrates), milk powder sources or mixtures thereof;

ingredients providing alpha-tocopherol in an amount ranging from 5 to 1800 µg/g or 1.25 to 450 µg/g or 1 to 360 µg/g of fortifier, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;

ingredients providing LNT in an amount ranging from 0.5 to 55 mg/g or 0.125 to 13.75 mg/g or 0.1 to 11 mg/g of fortifier, for example Lacto-N-tetraose;

ingredients providing 6'SL in an amount ranging from 5 to 55 mg/g or 1.25 to 13.75 mg/g or 1 to 11 mg/g of fortifier, for example 6'-sialyllactose.

In a further embodiment, a human milk fortifier is provided which further comprises ingredients providing LnNT in an amount ranging from 0.1 to 25 mg/g or 0.025 to 6.25 mg/g or 0.02 to 5 mg/g of fortifier, for example Lacto-N-neotetraose.

Human milk fortifier as stand alone composition (or supplement)

In certain embodiments of the present invention, the human milk fortifier may be administered as a stand alone composition (without being dissolved/reconstituted in human breast milk or in human breast milk already fortified with other nutrients). In such embodiments, the daily need for the claimed nutrients according to the present invention may be provided to the infants in a single administration or in the form of a supplement to be proposed at one or more feeding attempt.

Based on the results of the clinical trial reported in FIG. 3, on recommended milk intake volumes and on average body weight at different post menstrual ages, the scientists have derived the missing amounts for each of the nutrients claimed at discharge (for example between weeks 38 and 43 of post menstrual age) on a daily basis.

In the time window comprised between 38 and 43 weeks of post menstrual age, the range of missing alpha-lactalbumin amounts on a daily basis (from 0.41 to 1.31 g) has been derived as follows. The lower end for the range is calculated starting from missing amount of alpha lactalbumin in human breast milk of preterm mothers (as reported in FIG. 3, 1.07 g/L), assuming a daily intake of 170 ml/Kg of body weight (Amez et al, JPGN, 2010:50:200-7) and referring to the body weight of baby girls in the $3^{rd}$ percentile at 38 weeks (Fenton and Kim BMC Pediatrics 2013, 13:59). On the other hand, the higher end for the range is calculated starting from missing amount of alpha lactalbumin in human breast milk of preterm mothers (as reported in FIG. 3, 1.07 g/L), assuming a daily intake of 210 ml/Kg of body weight (Lucas et al, ADC, 1992-67-691-2) and referring to the body weight of baby girls in the $97^{th}$ percentile at 43 weeks (Fenton and Kim BMC Pediatrics 2013, 13:59).

Starting from the same elements (missing amount of a certain nutrient in preterm human breast milk, average daily intake per kg of body weight and body weight at a certain post menstrual age), the skilled person would also be able to contemplate different ways of calculating such ranges for the daily missing amounts of the claimed nutrients.

In a further embodiment, the present invention provides for human milk fortifier comprising at least one ingredient selected in the group consisting of:

ingredients providing copper in an amount ranging from 79 to 253 µg, or from 87 to 238 µg or from 107 to 202 µg, for example cupric carbonate, cupric citrate, cupric gluconate, cupric sulphate, cupric lysine complex or mixtures thereof;

ingredients providing selenium in an amount ranging from 1 to 7 µg or 2 to 6 µg or 2 to 5 µg, for example sodium selenite, sodium selenate, sodium hydrogen selenite or mixtures thereof;

ingredients providing zinc in an amount ranging from 1220 to 3880 µg or 1340 to 3640 µg or 1640 to 3090 µg, for example zinc acetate, zinc chloride, zinc citrate, zinc gluconate, zinc lactate, zinc oxide, zinc sulphate, zinc carbonate or mixtures thereof;

ingredients providing alpha-lactalbumin in an amount ranging from 0.4 to 1.31 or 0.45 to 1.23 g or 0.55 to 1.05 g, for example milk (e.g. whole or skimmed milk powder), whey protein (e.g. isolates or concentrates), milk powder sources or mixtures thereof;

ingredients providing caseins in an amount ranging from 0.82 to 2.60 g or 0.90 to 2.44 g or 1.10 to 2.07 g, for example milk (e.g. whole or skimmed milk powder), whey protein (e.g. isolates or concentrates), milk powder sources or mixtures thereof;

ingredients providing lactoferrin in an amount ranging from 0.50 to 1.58 g or 0.55 to 1.58 g or 0.67 to 1.26 g, for example purified or manufactured lactoferrin, whey protein isolate, whey protein concentrate or mixtures thereof;

ingredients providing alpha-tocopherol in an amount ranging from 2.39 to 7.60 mg or 2.64 to 7.13 g or 3.21 to 6.06 mg, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;

ingredients providing gamma-tocopherol in an amount ranging from 0.04 to 0.13 mg or 0.05 to 0.13 mg or 0.06 to 0.11 mg;

ingredients providing nicotinic acid in an amount ranging from 2.44 to 7.74 µg or 2.68 to 7.26 µg or 3.27 to 6.17 µg, for example nicotinic acid, nicotinamide or mixtures thereof;

ingredients providing retinol in an amount ranging from 0.24 to 0.75 mg or 0.26 to 0.70 mg or 0.32 to 0.60 mg, for example retinol, retinyl acetate, retinyl palmitate or mixtures thereof;

ingredients providing DFSLTHN in an amount ranging from 40 to 128 mg or 44 to 120 mg or 54 to 102 mg, for example Difucosyllacto-N-Hexaose-a;

ingredients providing FSLTNH3 in an amount ranging from 45 to 145 mg or 50 to 135 mg or 61 to 115 mg/g, for example Monofucosyllacto-N-hexaose-III;

ingredients providing GSLT6 in an amount ranging from 21 to 68 mg or 23 to 64 mg or 28 to 54 mg, for example 6'-galactosyllactose;

ingredients providing LnNT in an amount ranging from 47 to 151 mg or 52 to 142 mg or 64 to 120 mg, for example Lacto-N-neotetraose;

ingredients providing LNT in an amount ranging from 87 to 279 mg or 96 to 262 mg or 118 to 222 mg/g, for example Lacto-N-tetraose;

ingredients providing 6'SL in an amount ranging from 132 to 421 mg or from 146 to 395 mg or 178 to 336 mg, for example 6'-sialyllactose or 6'-sialyllactose sodium salt; and ingredients providing SLTNTC in an amount ranging from 139 to 443 mg or 153 to 415 mg or 187 to 353 mg, for example Sialyllactose-N-tetraose-c; Or mixtures thereof.

In another embodiment, the present invention provides for a human milk fortifier comprising at least one ingredient providing minerals and selected in the group consisting of:

ingredients providing copper in an amount ranging from 79 to 253 μg, or from 87 to 238 μg or from 107 to 202 μg, for example cupric carbonate, cupric citrate, cupric gluconate, cupric sulphate, cupric lysine complex or mixtures thereof;

ingredients providing selenium in an amount ranging from 1 to 7 μg or 2 to 6 μg or 2 to 5 μg, for example sodium selenite, sodium selenate, sodium hydrogen selenite or mixtures thereof;

ingredients providing zinc in an amount ranging from 1220 to 3880 μg or 1340 to 3640 μg or 1640 to 3090 μg, for example zinc acetate, zinc chloride, zinc citrate, zinc gluconate, zinc lactate, zinc oxide, zinc sulphate, zinc carbonate or mixtures thereof.

In another embodiment, the present invention provides for a human milk fortifier comprising at least one ingredient providing proteins and selected in the group consisting of:

ingredients providing alpha-lactalbumin in an amount ranging from 0.4 to 1.31 or 0.45 to 1.23 g or 0.55 to 1.05 g, for example milk (e.g. whole or skimmed milk powder), whey protein (e.g. isolates or concentrates), milk powder sources or mixtures thereof;

ingredients providing caseins in an amount ranging from 0.82 to 2.60 g or 0.90 to 2.44 g or 1.10 to 2.07 g, for example milk (e.g. whole or skimmed milk powder), whey protein (e.g. isolates or concentrates), milk powder sources or mixtures thereof;

ingredients providing lactoferrin in an amount ranging from 0.50 to 1.58 g or 0.55 to 1.58 g or 0.67 to 1.26 g, for example purified or manufactured lactoferrin, whey protein isolate, whey protein concentrate or mixtures thereof.

In another embodiment, the present invention provides for a human milk fortifier comprising at least one ingredient providing vitamins and selected in the group consisting of:

ingredients providing alpha-tocopherol in an amount ranging from 2.39 to 7.60 mg or 2.64 to 7.13 g or 3.21 to 6.06 mg, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;

ingredients providing gamma-tocopherol in an amount ranging from 0.04 to 0.13 mg or 0.05 to 0.13 mg or 0.06 to 0.11 mg;

ingredients providing nicotinic acid in an amount ranging from 2.44 to 7.74 μg or 2.68 to 7.26 μg or 3.27 to 6.17 μg, for example nicotinic acid, nicotinamide or mixtures thereof;

ingredients providing retinol in an amount ranging from 0.24 to 0.75 mg or 0.26 to 0.70 mg or 0.32 to 0.60 mg, for example retinol, retinyl acetate, retinyl palmitate or mixtures thereof.

In another embodiment, the present invention provides for a human milk fortifier comprising at least one ingredient providing human milk oligosaccharides and selected in the group consisting of:

ingredients providing DFSLTHN in an amount ranging from 40 to 128 mg or 44 to 120 mg or 54 to 102 mg, for example Difucosyllacto-N-Hexaose-a;

ingredients providing FSLTNH3 in an amount ranging from 45 to 145 mg or 50 to 135 mg or 61 to 115 mg/g, for example Monofucosyllacto-N-hexaose-III;

ingredients providing GSLT6 in an amount ranging from 21 to 68 mg or 23 to 64 mg or 28 to 54 mg, for example 6'-galactosyllactose;

ingredients providing LnNT in an amount ranging from 47 to 151 mg or 52 to 142 mg or 64 to 120 mg, for example Lacto-N-neotetraose;

ingredients providing LNT in an amount ranging from 87 to 279 mg or 96 to 262 mg or 118 to 222 mg/g, for example Lacto-N-tetraose;

ingredients providing 6'SL in an amount ranging from 132 to 421 mg or from 146 to 395 mg or 178 to 336 mg, for example 6'-sialyllactose or 6'-sialyllactose sodium salt; and ingredients providing SLTNTC in an amount ranging from 139 to 443 mg or 153 to 415 mg or 187 to 353 mg, for example Sialyllactose-N-tetraose-c.

In another embodiment, the present invention provides for human milk fortifier comprising:

ingredients providing zinc in an amount ranging from 1220 to 3880 mg or 1340 to 3640 mg or 1640 to 3090 μg, for example zinc acetate, zinc chloride, zinc citrate, zinc gluconate, zinc lactate, zinc oxide, zinc sulphate, zinc carbonate or mixtures thereof;

ingredients providing alpha-lactalbumin in an amount ranging from 0.4 to 1.31 or 0.45 to 1.23 g or 0.55 to 1.05 g, for example milk (e.g. whole or skimmed milk powder), whey protein (e.g. isolates or concentrates), milk powder sources or mixtures thereof;

ingredients providing caseins in an amount ranging from 0.82 to 2.60 g or 0.90 to 2.44 g or 1.10 to 2.07 g, for example milk (e.g. whole or skimmed milk powder), whey protein (e.g. isolates or concentrates), milk powder sources or mixtures thereof;

ingredients providing alpha-tocopherol in an amount ranging from 2.39 to 7.60 mg or 2.64 to 7.13 g or 3.21 to 6.06 mg, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;

ingredients providing LnNT in an amount ranging from 47 to 151 mg or 52 to 142 mg or 64 to 120 mg, for example Lacto-N-neotetraose.

In a further embodiment, the human milk fortifier according to the present invention further comprises ingredients providing LNT in an amount ranging from 87 to 279 mg or 96 to 262 mg or 118 to 222 mg/g, for example Lacto-N-tetraose.

In the embodiments above described, the human milk fortifier is in the form of a stand-alone composition which is administered to the infant once per day.

In a still further embodiment, the present invention provides for a human milk fortifier comprising at least one ingredient selected in the group consisting of:

- ingredients providing copper in an amount ranging from 26 to 84 μg, or from 29 to 79 μg or from 35 to 67 μg, for example cupric carbonate, cupric citrate, cupric gluconate, cupric sulphate, cupric lysine complex or mixtures thereof;
- ingredients providing selenium in an amount ranging from 0.33 to 2.33 μg or 0.66 to 2 μg or 0.66 to 1.66 μg, for example sodium selenite, sodium selenate, sodium hydrogen selenite or mixtures thereof;
- ingredients providing zinc in an amount ranging from 406 to 1293 μg or 447 to 1213 μg or 546 to 1030 μg, for example zinc acetate, zinc chloride, zinc citrate, zinc gluconate, zinc lactate, zinc oxide, zinc sulphate, zinc carbonate or mixtures thereof;
- ingredients providing alpha-lactalbumin in an amount ranging from 0.13 to 0.44 or 0.15 to 0.41 g or 0.18 to 0.35 g, for example milk (e.g. whole or skimmed milk powder), whey protein (e.g. isolates or concentrates), milk powder sources or mixtures thereof;
- ingredients providing caseins in an amount ranging from 0.27 to 0.87 g or 0.30 to 0.81 g or 0.37 to 0.69 g, for example milk (e.g. whole or skimmed milk powder), whey protein (e.g. isolates or concentrates), milk powder sources or mixtures thereof;
- ingredients providing lactoferrin in an amount ranging from 0.17 to 0.53 g or 0.18 to 0.53 g or 0.22 to 0.42 g, for example purified or manufactured lactoferrin, whey protein isolate, whey protein concentrate or mixtures thereof;
- ingredients providing alpha-tocopherol in an amount ranging from 0.80 to 2.53 mg or 0.88 to 2.38 g or 1.07 to 2.02 mg, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;
- ingredients providing gamma-tocopherol in an amount ranging from 0.013 to 0.04 mg or 0.016 to 0.04 mg or 0.02 to 0.037 mg;
- ingredients providing nicotinic acid in an amount ranging from 0.81 to 2.58 μg or 0.89 to 2.42 μg or 1.09 to 2.06 μg, for example nicotinic acid, nicotinamide or mixtures thereof;
- ingredients providing retinol in an amount ranging from 0.08 to 0.25 mg or 0.08 to 0.23 mg or 0.10 to 0.20 mg, for example retinol, retinyl acetate, retinyl palmitate or mixtures thereof;
- ingredients providing DFSLTHN in an amount ranging from 13 to 43 mg or 14 to 40 mg or 18 to 34 mg, for example Difucosyllacto-N-Hexaose-a;
- ingredients providing FSLTNH3 in an amount ranging from 15 to 48 mg or 16 to 45 mg or 20 to 39 mg/g, for example Monofucosyllacto-N-hexaose-III;
- ingredients providing GSLT6 in an amount ranging from 21 to 68 mg or 23 to 64 mg or 28 to 54 mg, for example 6'-galactosyllactose;
- ingredients providing LnNT in an amount ranging from 15 to 51 mg or 17 to 47 mg or 21 to 40 mg, for example Lacto-N-neotetraose;
- ingredients providing LNT in an amount ranging from 29 to 93 mg or 32 to 87 mg or 39 to 74 mg/g, for example Lacto-N-tetraose;
- ingredients providing 6'SL in an amount ranging from 44 to 140 mg or from 48 to 132 mg or 59 to 112 mg, for example 6'-sialyllactose or 6'-sialyllactose sodium salt; and
- ingredients providing SLTNTC in an amount ranging from 46 to 148 mg or 51 to 138 mg or 62 to 118 mg, for example Sialyllactose-N-tetraose-c; Or mixtures thereof.

In another embodiment, the present invention provides for a human milk fortifier comprising at least one ingredient providing minerals and selected in the group consisting of:

- ingredients providing copper in an amount ranging from 26 to 84 μg, or from 29 to 79 μg or from 35 to 67 μg, for example cupric carbonate, cupric citrate, cupric gluconate, cupric sulphate, cupric lysine complex or mixtures thereof;
- ingredients providing selenium in an amount ranging from 0.33 to 2.33 μg or 0.66 to 2 μg or 0.66 to 1.66 μg, for example sodium selenite, sodium selenate, sodium hydrogen selenite or mixtures thereof;
- ingredients providing zinc in an amount ranging from 406 to 1293 μg or 447 to 1213 μg or 546 to 1030 μg, for example zinc acetate, zinc chloride, zinc citrate, zinc gluconate, zinc lactate, zinc oxide, zinc sulphate, zinc carbonate or mixtures thereof.

In another embodiment, the present invention provides for a human milk fortifier comprising at least one ingredient providing proteins and selected in the group consisting of:

- ingredients providing alpha-lactalbumin in an amount ranging from 0.13 to 0.44 or 0.15 to 0.41 g or 0.18 to 0.35 g, for example milk (e.g. whole or skimmed milk powder), whey protein (e.g. isolates or concentrates), milk powder sources or mixtures thereof;
- ingredients providing caseins in an amount ranging from 0.27 to 0.87 g or 0.30 to 0.81 g or 0.37 to 0.69 g, for example milk (e.g. whole or skimmed milk powder), whey protein (e.g. isolates or concentrates), milk powder sources or mixtures thereof;
- ingredients providing lactoferrin in an amount ranging from 0.17 to 0.53 g or 0.18 to 0.53 g or 0.22 to 0.42 g, for example purified or manufactured lactoferrin, whey protein isolate, whey protein concentrate or mixtures thereof.

In another embodiment, the present invention provides for a human milk fortifier comprising at least one ingredient providing vitamins and selected in the group consisting of:

- ingredients providing alpha-tocopherol in an amount ranging from 0.80 to 2.53 mg or 0.88 to 2.38 g or 1.07 to 2.02 mg, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;
- ingredients providing gamma-tocopherol in an amount ranging from 0.013 to 0.04 mg or 0.016 to 0.04 mg or 0.02 to 0.037 mg;
- ingredients providing nicotinic acid in an amount ranging from 0.81 to 2.58 μg or 0.89 to 2.42 μg or 1.09 to 2.06 μg, for example nicotinic acid, nicotinamide or mixtures thereof;
- ingredients providing retinol in an amount ranging from 0.08 to 0.25 mg or 0.08 to 0.23 mg or 0.10 to 0.20 mg, for example retinol, retinyl acetate, retinyl palmitate or mixtures thereof.

In another embodiment, the present invention provides for a human milk fortifier comprising at least one ingredient providing human milk oligosaccharides and selected in the group consisting of:

ingredients providing DFSLTHN in an amount ranging from 13 to 43 mg or 14 to 40 mg or 18 to 34 mg, for example Difucosyllacto-N-Hexaose-a;

ingredients providing FSLTNH3 in an amount ranging from 15 to 48 mg or 16 to 45 mg or 20 to 39 mg/g, for example Monofucosyllacto-N-hexaose-III;

ingredients providing GSLT6 in an amount ranging from 21 to 68 mg or 23 to 64 mg or 28 to 54 mg, for example 6'-galactosyllactose;

ingredients providing LnNT in an amount ranging from 15 to 51 mg or 17 to 47 mg or 21 to 40 mg, for example Lacto-N-neotetraose;

ingredients providing LNT in an amount ranging from 29 to 93 mg or 32 to 87 mg or 39 to 74 mg/g, for example Lacto-N-tetraose;

ingredients providing 6'SL in an amount ranging from 44 to 140 mg or from 48 to 132 mg or 59 to 112 mg, for example 6'-sialyllactose or 6'-sialyllactose sodium salt; and ingredients providing SLTNTC in an amount ranging from 46 to 148 mg or 51 to 138 mg or 62 to 118 mg, for example Sialyllactose-N-tetraose-c.

In another embodiment, the present invention provides for a human milk fortifier comprising at least one ingredient selected in the group consisting of:

ingredients providing zinc in an amount ranging from 406 to 1293 µg or 447 to 1213 µg or 546 to 1030 µg, for example zinc acetate, zinc chloride, zinc citrate, zinc gluconate, zinc lactate, zinc oxide, zinc sulphate, zinc carbonate or mixtures thereof;

ingredients providing alpha-lactalbumin in an amount ranging from 0.13 to 0.44 or 0.15 to 0.41 g or 0.18 to 0.35 g, for example milk (e.g. whole or skimmed milk powder), whey protein (e.g. isolates or concentrates), milk powder sources or mixtures thereof;

ingredients providing caseins in an amount ranging from 0.27 to 0.87 g or 0.30 to 0.81 g or 0.37 to 0.69 g, for example milk (e.g. whole or skimmed milk powder), whey protein (e.g. isolates or concentrates), milk powder sources or mixtures thereof;

ingredients providing alpha-tocopherol in an amount ranging from 0.80 to 2.53 mg or 0.88 to 2.38 g or 1.07 to 2.02 mg, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;

ingredients providing LnNT in an amount ranging from 15 to 51 mg or 17 to 47 mg or 21 to 40 mg, for example Lacto-N-neotetraose.

In an additional embodiment, the present invention provides for a human milk fortifier further comprising:

ingredients providing LNT in an amount ranging from 29 to 93 mg or 32 to 87 mg or 39 to 74 mg/g, for example Lacto-N-tetraose.

In the embodiments above described, the human milk fortifier is in the form of a stand-alone composition which is administered to the infant three times per day.

In an additional embodiment, the present invention provides for human milk fortifier composition according to claim 1 comprising at least one ingredient selected in the group consisting of:

ingredients providing copper in an amount ranging from 39.5 to 127 µg, or from 43 to 119 mg or from 53 to 101 µg, for example cupric carbonate, cupric citrate, cupric gluconate, cupric sulphate, cupric lysine complex or mixtures thereof;

ingredients providing selenium in an amount ranging from 0.5 to 4 mg or 1 to 3 mg or 1 to 2.5 µg, for example sodium selenite, sodium selenate, sodium hydrogen selenite or mixtures thereof;

ingredients providing zinc in an amount ranging from 610 to 1940 µg or 670 to 1820 µg or 820 to 1545 µg, for example zinc acetate, zinc chloride, zinc citrate, zinc gluconate, zinc lactate, zinc oxide, zinc sulphate, zinc carbonate or mixtures thereof;

ingredients providing alpha-lactalbumin in an amount ranging from 0.2 to 0.66 or 0.22 to 0.62 g or 0.27 to 0.53 g, for example milk (e.g. whole or skimmed milk powder), whey protein (e.g. isolates or concentrates), milk powder sources or mixtures thereof;

ingredients providing caseins in an amount ranging from 0.41 to 1.30 g or 0.45 to 1.22 g or 0.55 to 1.04 g, for example milk (e.g. whole or skimmed milk powder), whey protein (e.g. isolates or concentrates), milk powder sources or mixtures thereof;

ingredients providing lactoferrin in an amount ranging from 0.25 to 0.79 g or 0.27 to 0.79 g or 0.33 to 0.63 g, for example purified or manufactured lactoferrin, whey protein isolate, whey protein concentrate or mixtures thereof;

ingredients providing alpha-tocopherol in an amount ranging from 1.19 to 3.80 mg or 1.32 to 3.57 g or 1.60 to 3.03 mg, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;

ingredients providing gamma-tocopherol in an amount ranging from 0.02 to 0.07 mg or 0.025 to 0.07 mg or 0.03 to 0.06 mg;

ingredients providing nicotinic acid in an amount ranging from 1.22 to 3.87 µg or 1.34 to 3.63 µg or 1.63 to 3.08 µg, for example nicotinic acid, nicotinamide or mixtures thereof;

ingredients providing retinol in an amount ranging from 0.12 to 0.37 mg or 0.13 to 0.35 mg or 0.16 to 0.30 mg, for example retinol, retinyl acetate, retinyl palmitate or mixtures thereof;

ingredients providing DFSLTHN in an amount ranging from 20 to 64 mg or 22 to 60 mg or 27 to 51 mg, for example Difucosyllacto-N-Hexaose-a;

ingredients providing FSLTNH3 in an amount ranging from 22 to 73 mg or 25 to 68 mg or 30 to 58 mg/g, for example Monofucosyllacto-N-hexaose-III;

ingredients providing GSLT6 in an amount ranging from 10 to 34 mg or 11 to 32 mg or 14 to 27 mg, for example 6'-galactosyllactose;

ingredients providing LnNT in an amount ranging from 23 to 76 mg or 26 to 71 mg or 32 to 60 mg, for example Lacto-N-neotetraose;

ingredients providing LNT in an amount ranging from 43 to 140 mg or 48 to 131 mg or 59 to 111 mg/g, for example Lacto-N-tetraose;

ingredients providing 6'SL in an amount ranging from 66 to 211 mg or from 73 to 198 mg or 89 to 168 mg, for example 6'-sialyllactose or 6'-sialyllactose sodium salt; and ingredients providing SLTNTC in an amount ranging from 68 to 222 mg or 76 to 208 mg or 93 to 177 mg, for example Sialyllactose-N-tetraose-c;

Or mixtures thereof.

In another embodiment, the present invention provides for human milk fortifier composition comprising at least one ingredient providing minerals and selected in the group consisting of:

- ingredients providing copper in an amount ranging from 13 to 42 µg, or from 14 to 40 mg or from 17 to 34 µg, for example cupric carbonate, cupric citrate, cupric gluconate, cupric sulphate, cupric lysine complex or mixtures thereof;
- ingredients providing selenium in an amount ranging from 0.165 to 1.165 mg or 0.33 to 1 mg or 0.33 to 0.84 µg, for example sodium selenite, sodium selenate, sodium hydrogen selenite or mixtures thereof;
- ingredients providing zinc in an amount ranging from 203 to 647 mg or 223 to 606 mg or 273 to 515 µg, for example zinc acetate, zinc chloride, zinc citrate, zinc gluconate, zinc lactate, zinc oxide, zinc sulphate, zinc carbonate or mixtures thereof;

Or mixtures thereof.

In a further embodiment, the present invention provides for human milk fortifier composition comprising at least one ingredient providing proteins and selected in the group consisting of:

- ingredients providing alpha-lactalbumin in an amount ranging from 0.06 to 0.22 or 0.07 to 0.21 g or 0.09 to 0.17 g, for example milk (e.g. whole or skimmed milk powder), whey protein (e.g. isolates or concentrates), milk powder sources or mixtures thereof;
- ingredients providing caseins in an amount ranging from 0.13 to 0.44 g or 0.15 to 0.41 g or 0.18 to 0.35 g, for example milk (e.g. whole or skimmed milk powder), whey protein (e.g. isolates or concentrates), milk powder sources or mixtures thereof;
- ingredients providing lactoferrin in an amount ranging from 0.08 to 0.27 g or 0.09 to 0.27 g or 0.11 to 0.21 g, for example purified or manufactured lactoferrin, whey protein isolate, whey protein concentrate or mixtures thereof; Or mixtures thereof.

In a further embodiment, the present invention provides for human milk fortifier composition comprising at least one ingredient providing vitamins and selected in the group consisting of:

- ingredients providing alpha-tocopherol in an amount ranging from 0.40 to 1.27 mg or 0.44 to 1.19 g or 0.54 to 1.01 mg, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;
- ingredients providing gamma-tocopherol in an amount ranging from 0.006 to 0.02 mg or 0.008 to 0.02 mg or 0.01 to 0.018 mg;
- ingredients providing nicotinic acid in an amount ranging from 0.40 to 1.29 mg or 0.44 to 1.21 mg or 0.54 to 1.03 µg, for example nicotinic acid, nicotinamide or mixtures thereof;
- ingredients providing retinol in an amount ranging from 0.04 to 0.13 mg or 0.04 to 0.12 mg or 0.05 to 0.10 mg, for example retinol, retinyl acetate, retinyl palmitate or mixtures thereof;

Or mixtures thereof.

In a further embodiment, the present invention provides for human milk fortifier composition comprising at least one ingredient providing human milk oligosaccharides and selected in the group consisting of:

- ingredients providing DFSLTHN in an amount ranging from 6 to 22 mg or 7 to 20 mg or 9 to 17 mg, for example Difucosyllacto-N-Hexaose-a;
- ingredients providing FSLTNH3 in an amount ranging from 7 to 24 mg or 8 to 23 mg or 10 to 20 mg/g, for example Monofucosyllacto-N-hexaose-III;
- ingredients providing GSLT6 in an amount ranging from 10 to 34 mg or 12 to 32 mg or 14 to 27 mg, for example 6'-galactosyllactose;
- ingredients providing LnNT in an amount ranging from 7 to 26 mg or 8 to 24 mg or 10 to 20 mg, for example Lacto-N-neotetraose;
- ingredients providing LNT in an amount ranging from 15 to 47 mg or 16 to 44 mg or 18 to 37 mg/g, for example Lacto-N-tetraose;
- ingredients providing 6'SL in an amount ranging from 22 to 70 mg or from 24 to 61 mg or 28 to 56 mg, for example 6'-sialyllactose or 6'-sialyllactose sodium salt; and
- ingredients providing SLTNTC in an amount ranging from 23 to 74 mg or 25 to 69 mg or 31 to 59 mg, for example Sialyllactose-N-tetraose-c;

Or mixtures thereof.

In a further embodiment, the present invention provides for human milk fortifier comprising:

- ingredients providing zinc in an amount ranging from 203 to 647 µg or 223 to 606 µg or 273 to 515 µg, for example zinc acetate, zinc chloride, zinc citrate, zinc gluconate, zinc lactate, zinc oxide, zinc sulphate, zinc carbonate or mixtures thereof;
- ingredients providing alpha-lactalbumin in an amount ranging from 0.06 to 0.22 or 0.07 to 0.21 g or 0.09 to 0.17 g, for example milk (e.g. whole or skimmed milk powder), whey protein (e.g. isolates or concentrates), milk powder sources or mixtures thereof;
- ingredients providing caseins in an amount ranging from 0.13 to 0.44 g or 0.15 to 0.41 g or 0.18 to 0.35 g, for example milk (e.g. whole or skimmed milk powder), whey protein (e.g. isolates or concentrates), milk powder sources or mixtures thereof;
- ingredients providing alpha-tocopherol in an amount ranging from 0.40 to 1.27 mg or 0.44 to 1.19 g or 0.54 to 1.01 mg, for example D-alpha tocopherol, DL-alpha tocopherol, D-alpha tocopheryl acetate, DL-alpha tocopheryl acetate, DL-alpha tocopheryl succinate, DL-alpha tocopheryl polyethylene glycol 1000 succinate or mixtures thereof;
- ingredients providing LnNT in an amount ranging from 7 to 26 mg or 8 to 24 mg or 10 to 20 mg, for example Lacto-N-neotetraose;

Or mixtures thereof.

In an additional embodiment, the invention provides a human milk fortifier further comprising
ingredients providing LNT in an amount ranging from 15 to 47 mg or 16 to 44 mg or 18 to 37 mg/g, for example Lacto-N-tetraose.

In the embodiments above described, the human milk fortifier is in the form of a stand-alone composition which is administered to the infant six times per day.

Other Ingredients

In one embodiment of the present invention, the human milk fortifier composition according to the present invention doesn't comprise other ingredients beyond those providing the at least one nutrient selected in the group consisting of the above mentioned minerals, vitamins, milk proteins and human milk oligosaccharides.

In such embodiment, the human milk fortifier composition according to the present invention presents the additional advantage of having a high nutrient/energy ratio and/or low energy density. By virtue of such limited contribution to the energy content of human breast milk fortified according to the present invention, no consequent regulation of intake volumes is expected in the infants receiving such fortified human breast milk so that the maximum possible intake of nutrients may be achieved and the gap between preterm and term human breast milk in certain nutrients may be fully filled.

In such embodiment, the human milk fortifier of the present invention provides energy to 100 mL of human breast milk to be fortified in an amount ranging from 0 to 4.57 Kcal.

In one embodiment, the human milk fortifier of the present invention has an energy content ranging from 0 to 4.57 Kcal/g of fortifier, for example ranging from 0 to 2.5 Kcal/g of fortifier. In such embodiment the unit dose of the fortifier is 1 g of fortifier/100 mL of milk to be fortified.

In another embodiment, the human milk fortifier of the present invention has an energy content ranging from 0 to 1.1 Kcal/g of fortifier. In such embodiment the unit dose of the fortifier is 4 g of fortifier/100 mL of milk to be fortified.

In a further embodiment, the human milk fortifier of the present invention has an energy content ranging from 0 to 0.9 Kcal/g of fortifier. In such embodiment the unit dose of the fortifier is 5 g of fortifier/100 mL of milk to be fortified.

In another embodiment, the human milk fortifier composition, according to the present invention could, besides from comprising at least one nutrient selected in the group consisting of the above mentioned minerals, vitamins, milk proteins and human milk oligosaccharides, optionally comprise also other additional and different nutrients as e.g. carbohydrates, probiotics, lipids, other vitamins or minerals.

If necessary, the composition according to the present invention may comprise emulsifiers and/or stabilizers such as lecithin, citric esters of mono- and diglycerides, monoglycerides, diglycerides and the like. This is especially the case if the composition is provided as a combination of oils and an aqueous liquid, e.g. as an emulsion.

The composition may also optionally comprise other substances which may have a beneficial effect such as nucleotides, nucleosides, and the like in the amount customarily found in nutritional compositions to be fed to infants.

Other optional ingredients may be ones normally known for use on food and nutritional products, in particular infant formulas or infant formula fortifiers, provided that such optional materials are compatible with the essential components described herein, are safe and effective for their intended se, and do not otherwise unduly impair product performance.

Non-limiting examples of such optional ingredients include preservatives, probiotics, anti-oxidants, buffers, colorants, flavours, thickening agents, stabilizers, and other excipients or processing aids.

Use of the Human Milk Fortifier

The quality and the amount of various nutrients an infant receives can impact numerous health parameters.

Milk proteins, human milk oligosaccharides, minerals, vitamins are all considered necessary for optimal growth and development in an infant. Thus, optimizing their quality and content in infants' nutrition (especially for infants born preterm, VLBW and/or ELBW) as provided in the context of the present invention may prevent sub-optimal growth and development (including preventing and/or treating growth stunting, infection, lung disease, suboptimal nutritional status, anaemia, (neuro) developmental delays, blindness and bone metabolic disease) and may promote optimal growth and development.

In one embodiment of the present invention, a human milk fortifier composition is provided for use in fortifying human breast milk of mothers who gave birth preterm at the time of discharge from the hospital of the infant who was born preterm and afterwards.

In another embodiment of the present invention, a human milk fortifier composition is provided for use in fortifying human breast milk of mothers who gave birth to VLBW or ELBW infants at the time of discharge from the hospital of the infant who was born VLBW or ELBW and afterwards.

Preterm infants are in fact particularly at risk of growth stunting, infection, lung disease, suboptimal nutritional status, anaemia, (neuro) developmental delays, blindness and bone metabolic disease after being discharged from the hospital.

In a further embodiment of the present invention, a human milk fortifier composition is provided for use in prevention and/or treatment of a condition selected in the group consisting of: stunting of growth, infection, lung disease, developmental delays, blindness and/or bone metabolic disease.

In a still further embodiment, the present invention provides a human milk fortifier composition for use in prevention and/or treatment of a condition selected in the group consisting of: sub-optimal growth and/or development, stunting of growth, infection, lung disease, developmental delays, blindness and/or bone metabolic disease; for administration at the time of discharge from the hospital (and after) of the infant who was born preterm, VLBW or ELBW.

Preparation:

The composition according to the present invention may be prepared in any suitable manner. For example, a composition may be prepared by blending together the ingredients in appropriate proportions. If used, emulsifiers may be included in the blend at this stage. The vitamins and minerals may be added at this stage but are usually added later to avoid thermal degradation. Water, preferably water which has been subjected to reverse osmosis, may then be mixed in to a liquid mixture.

A still further aspect of the invention relates to a package comprising the composition according to the invention, wherein the package is a single-dosing device or a multi-dosing device.

In a specific embodiment of the invention, the package is a syringe, pouch, stick pack, or bottle.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

Experimental Section

Example 1: Comparison of Breast Milk from Mothers Delivering Prematurely with Milk of Mothers Delivering at Term In the present study the content of breast milk of mothers delivering prematurely was compared in terms of several nutrients with the content of breast milk of mothers delivering at term. The comparison was performed over a period ranging from 38 to 48 weeks of babies' post menstrual age.

Methods Used for Breast Milk Analysis

Minerals:

Copper (Cu), Selenium (Se) and Zinc (Zn) were analysed according to the following method: 0.0.7 mL of breast milk were transferred into PFA vessels and mineralized in a CEM Microwave digestion system using Nitric acid ($HNO_3$)/Hydrogen peroxide ($H_2O_2$). Mineralized samples were transferred to PE tubes and diluted to 15 mL using Millipore water. Samples were then re-diluted after addition of Germanium (Ge) and Tellurium (Te) as internal standard and analyzed by Inductively Coupled Plasma Mass Spectrometry (ICP-MS, Nexion 300 D, Perkin Elmer). A Quality Control (QC) sample was included in the analysis.

Vitamins:

B-vitamins were analyzed according to reference Redeuil et al, (2017) "A Novel Methodology for the Quantification of B-Vitamers in Breast Milk". J Anal Bioanal Tech 8: 352. doi: 10.4172/2155-9872.1000352.

The analysis of vitamin A (carotenoids) and vitamin E (tocopherols) was performed according to the following method: vitamin E (α-tocopherol and γ-tocopherol), provitamin A carotenoids (β-carotene and β-cryptoxanthin), as well as other carotenoids such as lycopene, lutein and zeaxanthin in human milk were extracted by ethanolic protein precipitation and liquid-liquid extraction with a mixture of n-hexane and ethyl acetate containing butylated hydroxytoluene (BHT). The extracts were then evaporated to dryness under a nitrogen stream. The dried extracts were re-dissolved in isooctane-ethyl acetate and analysis was performed by Ultra High Performance Liquid Chromatography with UV/Visible or fluorimetric detection (UHPLC-UV-FLD, Waters Acquity UPLC; Thermo Hypersil GOLD Silica column, 1.9 μm, 200×2.1 mm). Analytes were quantified by external calibration using authentic standards, rac-tocol (Matreya LLC, 1797; CAS No 119-98-2) and trans-β-apo-8'-carotenal (Sigma-Aldrich, 10810; CAS No 1107-26-2).

HMOs (Austin et al. (2018) "Quantitative determination of non-lactose milk oligosaccharides" Analytica Chimica Acta 1010: 86. doi: 10.1016/j.aca.2017.12.036):

Oligosaccharides: Maltotriose was obtained from Sigma-Aldrich. Laminaritriose was obtained from Carbosynth Limited (Compton UK). A-tetrasaccharide (A-Tetra), 2'-fucosyllactose (2'FL), 3-fucosyllactose (3FL), Lacto-N-tetraose (LNT), Lacto-N-neotetraose (LNnT or LnNT), Lacto-N-neohexaose (LNnH), 3'-sialyllactose (3'SL), 6'-siayllactose (6'SL), Lacto-N-fucosylpentaose-I (LNFP-I), LNFP-V, Lacto-N-neofucosylpentaose-V (LNnFP-V) and Lacto-N-neodifucosylhexaose (LNnDFH) were obtained from Elicityl SA (Crolles, France). 3'-Galactosyllactose (3'GL), 6'-galactosyllactose (6'GL or GSLT6), 4'-galactosyllactose (4'GL), lacto-N-difucosylhexaose-I (LNDFH-I), difucosyllacto-N-hexaose-a (DFLNHa or DFSLTNH), disialyllacto-N-tetraose (DSLNT), monofucosyllacto-N-hexaose-III (MFLNH-III or FSLTNH3), LNFP-II, LNFP-III, sialyllacto-N-tetraose-a (LSTa), LSTb, LSTc and lacto-N-hexaose (LNH) were obtained from Dextra Laboratories Ltd (Reading, UK)

Sample Preparation: The milk sample or mixed standard solution (50 μL) was transferred to a microtube (1.5-mL) and laminaritriose solution (0.5 mM, 50 μL) was added. After mixing, an aliquot (20 μL) was transferred to another microtube (1.5 mL) and 2AB labelling reagent was added (2AB (0.35 M)+sodium cyanoborohydride (1 M) in DMSO/acetic acid (7/3), 200 μL). After mixing, the sample or standard was heated at 65° C. for 2 h. The mixture was then cooled at 4° C. for 10 min prior to adding a water/acetonitrile mixture (25/75, 0.6 mL). Particles were removed by centrifugation (10000×g, 5 min) prior to transferring samples or standards to the LC system.

Liquid Chromatography: An Ultimate 3000-RS ultra-high performance liquid chromatography (UHPLC) system equipped with an RF-2000 fluorimeter (FLD) and a 2-way 10 port high pressure switching valve (all from Thermo Fisher Scientific, Waltham, USA). The columns were an Acquity BEH Glycan (1.7 μm, 2.1×150 mm) and VanGuard BEH amide (1.7 μm, 2.1×50 mm) both from Waters Corporation (Milford, USA). The guard column was installed between injector and the 10-port valve. After injection, the sample was directed to the guard column with flow diverted to the waste to remove excess labelling reagents (0-2.3 min of gradient in table below), then the flow was directed through the analytical column and the oligosaccharides eluted using a gradient of ammonium formate (see table below). The flow rate was 0.5 mL min-1 and the analytical column was kept at 55° C. Detection was performed using a fluorimeter with excitation wavelength 330 nm and emission wavelength 420 nm.

| Time (min) | % Acetonitrile | % Ammonium Formate (50 mM) | Valve Position |
|---|---|---|---|
| 0 | 95 | 5 | Waste |
| 2.3 | 95 | 5 | Waste |
| 2.5 | 90 | 10 | Analysis |
| 4.9 | 90 | 10 | Analysis |
| 32.1 | 82 | 18 | Analysis |
| 48.1 | 80.5 | 19.5 | Analysis |
| 61.5 | 78.0 | 22.0 | Analysis |
| 89.0 | 74.6 | 25.4 | Analysis |
| 89.5 | 30 | 70 | Analysis |
| 92.0 | 30 | 70 | Analysis |
| 93.0 | 90 | 10 | Analysis |
| 98.0 | 90 | 10 | Analysis |
| 99.0 | 95 | 5 | Waste |
| 100 | 95 | 5 | Waste |

Proteins:

The individual proteins in human milk were analysed using the LabChip system as described in Affolter M, et al. (2016) "Temporal Changes of Protein Composition in Breast Milk of Chinese Urban Mothers and Impact of Caesarean Section Delivery. Nutrients" 2016, 8, 504; doi:10.3390.

Amino Acids:

Amino acids were analyzed according to the AccQ-Tag method from Waters (Waters Corporation, Milford, Mass., USA). Initially, proteins were hydrolyzed with 6 M HCl for 24 h at 110° C. Phenol (0.1%) was added to prevent halogenation of tyrosine. After hydrolysis and neutralization, amino acids were derivatized with 6-aminoquinolyl-N-hydroxysuccinimidyl carbamate (AQC) and then separated using reversed phase UHPLC with UV detection at 260 nm. During acid hydrolysis, glutamine (Gln) and asparagine (Asn) are converted to glutamic acid (Glu) and aspartic acid (Asp), thus Glu values represent the combined values of Glu and Gln, and Asp values represent the combined values of Asp and Asn.

Statistical Analysis:

All statistical analyses were done with the statistical software R 3.2.3.

This particular analysis combines all observations across the lifespan of the trial (max 12 observations for preterm infants and max 8 for term infants).

A mixed linear model was used in comparing the two groups (PRETERM and TERM) in which the group and mode of delivery was considered as fixed effects. The "within subject" variability is taken into account by declaring the subjects as random effects. The main point of comparison is PRETERM vs TERM infants. The adjustment for mode of delivery is there because it is a confounding effect with term status given that there are higher proportion of preterm infants delivered by c-section. A logarithmic transformation was applied to the HMO concentrations when modelling as the distribution is generally skewed and according to Box-Cox and QQ plots a log-transformation seems adequate. Only 2'FL was not transformed as its distribution can be assumed normal.

Results

Significant different amounts of several proteins, vitamins, minerals and human milk oligosaccharides were measured in breast milk of mothers delivering prematurely when compared with term milk according to corresponding post menstrual age of 38 to 48 weeks.

Results obtained for such nutrients are reported in FIG. 2.

For each nutrient, results reported in FIG. 2 represent average values registered over weeks 38 to 48 postmenstrual age. Of note, only those nutrients where the difference between average value for term and preterm resulted to be statistically significant (p<0.05) have been included in the table.

Additionally, FIG. 3 reports the same kind of analysis conducted over weeks 38 to 43. As it can be understood from the data shown in such table, the needs in terms of certain nutrients is particularly high in this period for preterm babies fed with the human milk coming from their mothers.

For each nutrient, results reported in FIG. 3 represent average values registered over weeks 38 to 43 postmenstrual age. Of note, only those nutrients where the difference between average value for term and preterm resulted to be statistically significant (p<0.05) have been included in the table.

FIG. 4 reports results of amino acids' analysis carried out on human breast milk samples collected between weeks 38 and 42 of post menstrual age (samples from 74 term and 29 preterm mothers). This analysis was carried out with the aim of alternative ingredients which could compensate for the lack of certain proteins (alpha-lactalbumin, caseins, lactoferrin) in preterm human breast milk as above explained.

The results indicate that there is a nutrient gap to be filled in the milk of mothers who gave birth to preterm infants in relation to the following amino acids: Glu (Glutamic acid), Pro (Proline), His (Histidine), Ile (Isoleucine), Leu (Leucine), Lys (Lysine), Met (Methionine), Trp (Tryptophan).

The amino acids where the difference between average value for term and preterm resulted to be clearly statistically significant (p<0.05) are: Ile, Leu, Met, Pro.

The analysis of amino acids also revealed statistically significant difference between term and preterm average value for the sum of essential amino acids [His, Ile, Leu, Lys, Met, Phe (Phanylalanine), Thr (Threonine), Trp, Val (Valine)].

These data represent the knowledge of the inventors at the time of filing.

In the light of the significant lower amount of the nutrients reported in FIG. 2 in preterm milk, it results that a preterm infant that is exclusively breastfed receives at the time of discharge from hospital (38 to 48 weeks) a significant lower amount of those nutrients as compared to a term infant of a corresponding post-menstrual age who is exclusively breastfed. As preterm infants already had a difficult start into life, optimal nutrition if of utmost importance and the results obtained in this study demonstrate the need to fortify the breast milk of preterm mothers in order to fill the gap in nutrients at discharge and promote growth and development in those premature infants.

Example 2

An example of a human milk fortifier composition according to the present invention is given below in Table 1. For the fortifier below described, the recommended unit dose is of 1 g of fortifier for 100 mL of human breast milk to be fortified

| Nutrient | Content in the Fortifier |
|---|---|
| alpha-lactalbumin | 92 mg |
| caseins | 148 mg |
| lactoferrin | 72 mg |
| copper | 17 µg |
| Selenium | 0.33 µg |
| Zinc | 229 µg |
| total tocopherol | 334 µg |
| alpha-tocopherol | 330 µg |
| gamma-tocopherol | 4 µg |
| VitA/Retinol | 35 µg |
| Nicotinic acid | 2.30 µg |
| DFSLTNH | 12 mg |
| FSLTNH3 | 14 mg |
| GSLT6 | 3 mg |
| LnNT | 7 mg |
| LNT | 22 mg |
| 6-SL | 26 mg |
| SLTNTC | 23 mg |
| Other ingredients | Summing up to 1 g of composition |

The composition according to the present invention may be fed to an infant at discharge from hospital as a fortifier for human breast milk.

The composition is particularly suitable for being fed to an infant who was born prematurely, as a supplement to human breast milk at the time of discharge or after, for example between 36 weeks and 9 months of post menstrual age.

The composition according to the present invention may be formulated with many variations without departing from the scope of the invention as defined in the claims.

The present invention also provides for the following embodiments:

a) A human milk fortifier composition comprising at least one ingredient selected in the group consisting of:
 ingredients providing copper;
 ingredients providing selenium;
 ingredients providing zinc;
 ingredients providing alpha-lactalbumin;
 ingredients providing casein;
 ingredients providing lactoferrin;
 ingredients providing alpha-tocopherol;
 ingredients providing gamma-tocopherol;
 ingredients providing nicotinic acid;
 ingredients providing retinol;
 ingredients providing DFSLTHN;
 ingredients providing FSLTNH3;
 ingredients providing; 6'-SL ingredients providing LnNT;
ingredients providing LNT;
ingredients providing 6'SL; and
ingredients providing SLTNTC;
Or mixtures thereof.

b) A human milk fortifier composition according to embodiment a) for reconstitution in human breast milk comprising at least one ingredient selected in the group consisting of:
- ingredients providing copper in an amount ranging from 5 to 30 μg/100 mL, for example 8 to 28 μg/100 mL, of human breast milk to be fortified;
- ingredients providing selenium in an amount ranging from 0.1 to 10 μg/100 mL, for example 0.3 to 8 μg/100 mL, of human breast milk to be fortified;
- ingredients providing zinc in an amount ranging from 50 to 550 μg/100 mL, for example 100 to 500 μg/100 mL, of human breast milk to be fortified;
- ingredients providing alpha-lactalbumin in an amount ranging from 25 to 180 mg/100 mL, for example 30 to 150 mg/100 mL, of human breast milk to be fortified;
- ingredients providing casein in an amount ranging from 10 to 500 mg/100 mL, for example 20 to 400 mg 100 mL, of human breast milk to be fortified;
- ingredients providing lactoferrin in an amount ranging from 10 to 500 mg/100 mL, for example 20 to 400 mg/100 mL, of human breast milk to be fortified;
- ingredients providing alpha-tocopherol in an amount ranging from 5 to 1800 μg/100 mL, for example 10 to 1700 μg/100 mL, of human breast milk to be fortified;
- ingredients providing gamma-tocopherol in an amount ranging from 0.1 to 50 μg/100 mL, for example 0.2 to 40 μg/100 mL, of human breast milk to be fortified;
- ingredients providing nicotinic acid in an amount ranging from 0.5 to 18 μg/100 mL, for example 1 to 15 μg/100 mL, of human breast milk to be fortified;
- ingredients providing retinol in an amount ranging from 1 to 250 μg/100 mL, for example 5 to 200 μg/100 mL, of human breast milk to be fortified;
- ingredients providing DFSLTHN in an amount ranging from 5 to 25 mg/100 mL, for example 8 to 15 mg/100 mL, of human breast milk to be fortified;
- ingredients providing FSLTNH3 in an amount ranging from 0.5 to 35 mg/100 mL, for example 5 to 20 mg/100 mL, of human breast milk to be fortified;
- ingredients providing GSLT6 in an amount ranging from 0.1 to 10 mg/100 mL, for example 1 to 5 mg/100 mL, of human breast milk to be fortified;
- ingredients providing LnNT in an amount ranging from 0.1 to 25 mg/100 mL, for example 1 to 10 mg/100 mL, of human breast milk to be fortified;
- ingredients providing LNT in an amount ranging from 0.5 to 55 mg/100 mL, for example 5 to 30 mg/100 mL, of human breast milk to be fortified;
- ingredients providing 6'SL in an amount ranging from 5 to 355 mg/100 mL, for example 15 to 35 mg/100 mL, of human breast milk to be fortified; and
- ingredients providing SLTNTC in an amount ranging from 1 to 60 mg/100 mL, for example 1 to 30 mg/100 mL, of human breast milk to be fortified; Or mixtures thereof.

c) A human milk fortifier composition according to embodiment a) or b) for reconstitution in human breast milk comprising at least one ingredient providing minerals and selected in the group consisting of:
- ingredients providing copper in an amount ranging from 5 to 30 μg/100 mL, for example 8 to 28 μg/100 mL, of human breast milk to be fortified;
- ingredients providing selenium in an amount ranging from 0.1 to 10 μg/100 mL, for example 0.3 to 8 μg/100 mL, of human breast milk to be fortified;
- ingredients providing zinc in an amount ranging from 50 to 550 μg/100 mL, for example 100 to 500 μg/100 mL, of human breast milk to be fortified;
Or mixtures thereof.

d) A human milk fortifier composition according to embodiment a) or b) for reconstitution in human breast milk comprising at least one ingredient providing milk proteins and selected in the group consisting of:
- ingredients providing alpha-lactalbumin in an amount ranging from 25 to 180 mg 100 mL, for example 30 to 150 mg/100 mL, of human breast milk to be fortified;
- ingredients providing casein in an amount ranging from 10 to 500 mg/100 mL, for example 0.02 to 0.4 μg/100 mL, of human breast milk to be fortified;
- ingredients providing lactoferrin in an amount ranging from 10 to 500 mg/100 mL, for example 20 to 400 mg/100 mL, of human breast milk to be fortified;
Or mixtures thereof.

e) A human milk fortifier composition according to embodiment a) or b) for reconstitution in human breast milk comprising at least one ingredient providing vitamins and selected in the group consisting of:
- ingredients providing alpha-tocopherol in an amount ranging from 5 to 1800 μg/100 mL, for example 10 to 1700 μg/100 mL, of human breast milk to be fortified;
- ingredients providing gamma-tocopherol in an amount ranging from 0.1 to 50 μg/100 mL, for example 0.2 to 40 μg/100 mL, of human breast milk to be fortified;
- ingredients providing nicotinic acid in an amount ranging from 0.5 to 18 μg/100 mL, for example 1 to 15 μg/100 mL, of human breast milk to be fortified;
- ingredients providing retinol in an amount ranging from 1 to 250 μg/100 mL, for example 5 to 200 μg/100 mL, of human breast milk to be fortified;
Or mixtures thereof.

f) A human milk fortifier composition according to embodiment a) or b) for reconstitution in human breast milk comprising at least one ingredient providing human milk oligosaccharides and selected in the group consisting of:
- ingredients providing DFSLTHN in an amount ranging from 5 to 25 mg/100 mL, for example 8 to 15 mg/100 mL, of human breast milk to be fortified;
- ingredients providing FSLTNH3 in an amount ranging from 0.5 to 35 mg/100 mL, for example 5 to 20 mg/100 mL, of human breast milk to be fortified;
- ingredients providing GSLT6 in an amount ranging from 0.1 to 10 mg/100 mL, for example 1 to 5 mg/100 mL, of human breast milk to be fortified;
- ingredients providing LnNT in an amount ranging from 0.1 to 25 mg/100 mL, for example 1 to 10 mg/100 mL, of human breast milk to be fortified;
- ingredients providing LNT in an amount ranging from 0.5 to 55 mg/100 mL, for example 5 to 30 mg/100 mL, of human breast milk to be fortified;
- ingredients providing 6'SL in an amount ranging from 5 to 355 mg/100 mL, for example 15 to 35 mg/100 mL, of human breast milk to be fortified; and
- ingredients providing SLTNTC in an amount ranging from 1 to 60 mg/100 mL, for example 1 to 30 mg/100 mL, of human breast milk to be fortified;
Or mixtures thereof.

g) A human milk fortifier composition according to embodiment a) comprising at least one ingredient selected in the group consisting of:
- ingredients providing copper in an amount ranging from 5 to 30 µg/g or 1.5 to 7.50 µg/g or 1 to 6 µg/g of fortifier;
- ingredients providing selenium in an amount ranging from 0.1 to 10 µg/g or 0.0025 to 25 µg/g or 0.002 to 0.2 µg/g of fortifier;
- ingredients providing zinc in an amount ranging from 50 to 550 µg/g or 12.5 to 137.5 µg/g or 10 to 110 µg/g of fortifier;
- ingredients providing alpha-lactalbumin in an amount ranging from 25 to 180 mg/g or 6.25 to 45 mg/g or 5 to 30 mg/g of fortifier;
- ingredients providing caseins in an amount ranging from 10 to 500 mg/g or 2.5 to 125 mg/g or 2 to 100 mg/g of fortifier;
- ingredients providing lactoferrin in an amount ranging from 10 to 500 mg/g or 2.5 to 125 mg/g or 2 to 100 mg/g of fortifier;
- ingredients providing alpha-tocopherol in an amount ranging from 5 to 1800 µg/g or 1.25 to 450 µg/g or 1 to 360 µg/g of fortifier;
- ingredients providing gamma-tocopherol in an amount ranging from 0.1 to 50 µg/g or 0.025 to 12.5 µg/g or 0.02 to 10 µg/g of fortifier;
- ingredients providing nicotinic acid in an amount ranging from 0.5 to 18 µg/g or 0.25 to 4.25 µg/g or 0.1 to 3.6 µg/g of fortifier;
- ingredients providing retinol in an amount ranging from 1 to 250 µg/g or 0.25 to 62.5 µg/g or 0.2 to 50 µg/g of fortifier;
- ingredients providing DFSLTHN in an amount ranging from 5 to 25 mg/g or 1.25 to 6.25 mg/g or 1 to 5 mg/g of fortifier;
- ingredients providing FSLTNH3 in an amount ranging from 0.5 to 35 mg/g or 0.125 to 8.75 mg/g or 0.1 to 7 mg/g of fortifier;
- ingredients providing GSLT6 in an amount ranging from 0.1 to 10 mg/g or 0.025 to 2.5 mg/g or 0.02 to 2 mg/g of fortifier;
- ingredients providing LnNT in an amount ranging from 0.1 to 25 mg/g or 0.025 to 6.25 mg/g or 0.02 to 5 mg/g of fortifier;
- ingredients providing LNT in an amount ranging from 0.5 to 55 mg/g or 0.125 to 13.75 mg/g or 0.1 to 11 mg/g of fortifier;
- ingredients providing 6'SL in an amount ranging from 5 to 55 mg/g or 1.25 to 13.75 mg/g or 1 to 11 mg/g of fortifier; and
- ingredients providing SLTNTC in an amount ranging from 1 to 60 mg/g or 0.25 to 15 mg/g or 0.2 to 12 mg/g of fortifier; Or mixtures thereof.

h) A human milk fortifier composition according to embodiments a) to g) comprising at least one ingredient providing minerals and selected in the group consisting of:
- ingredients providing copper in an amount ranging from 5 to 30 µg/g or 1.5 to 7.50 µg/g or 1 to 6 µg/g of fortifier;
- ingredients providing selenium in an amount ranging from 0.1 to 10 µg/g or 0.0025 to 25 µg/g or 0.002 to 0.2 µg/g of fortifier;
- ingredients providing zinc in an amount ranging from 50 to 550 µg/g or 12.5 to 137.5 µg/g or 10 to 110 µg/g of fortifier;
Or mixtures thereof.

i) A human milk fortifier composition according to embodiments a) to g) comprising at least one ingredient providing milk proteins and selected in the group consisting of:
- ingredients providing alpha-lactalbumin in an amount ranging from 25 to 180 mg/g or 6.25 to 45 mg/g or 5 to 30 mg/g of fortifier;
- ingredients providing caseins in an amount ranging from 10 to 500 mg/g or 2.5 to 125 mg/g or 2 to 100 mg/g of fortifier;
- ingredients providing lactoferrin in an amount ranging from 10 to 50 mg/g or 2.5 to 125 mg/g or 2 to 100 mg/g of fortifier;
Or mixtures thereof.

l) A human milk fortifier composition according to embodiments a) to g) comprising at least one ingredient providing vitamins and selected in the group consisting of:
- ingredients providing alpha-tocopherol in an amount ranging from 5 to 1800 µg/g or 1.25 to 450 µg/g or 1 to 360 µg/g of fortifier;
- ingredients providing gamma-tocopherol in an amount ranging from 0.1 to 50 µg/g or 0.025 to 12.5 µg/g or 0.02 to 10 µg/g of fortifier;
- ingredients providing nicotinic acid in an amount ranging from 0.5 to 18 µg/g or 0.25 to 4.25 µg/g or 0.1 to 3.6 µg/g of fortifier;
- ingredients providing retinol in an amount ranging from 1 to 250 µg/g or 0.25 to 62.5 µg/g or 0.2 to 50 µg/g of fortifier;
Or mixtures thereof.

m) A human milk fortifier composition according to embodiments a) to g) comprising at least one ingredient providing human milk oligosaccharides and selected in the group consisting of:
- ingredients providing DFSLTHN in an amount ranging from 5 to 25 mg/g or 1.25 to 6.25 mg/g or 1 to 5 mg/g of fortifier;
- ingredients providing FSLTNH3 in an amount ranging from 0.5 to 35 mg/g or 0.125 to 8.75 mg/g or 0.1 to 7 mg/g of fortifier;
- ingredients providing GSLT6 in an amount ranging from 0.1 to 10 mg/g or 0.025 to 2.5 mg/g or 0.02 to 2 mg/g of fortifier;
- ingredients providing LnNT in an amount ranging from 0.1 to 25 mg/g or 0.025 to 6.25 mg/g or 0.02 to 5 mg/g of fortifier;
- ingredients providing LNT in an amount ranging from 0.5 to 55 mg/g or 0.125 to 13.75 mg/g or 0.1 to 11 mg/g of fortifier;
- ingredients providing 6'SL in an amount ranging from 5 to 55 mg/g or 1.25 to 13.75 mg/g or 1 to 11 mg/g of fortifier; and
- ingredients providing SLTNTC in an amount ranging from 1 to 60 mg/g or 0.25 to 15 mg/g or 0.2 to 12 mg/g of fortifier;
Or mixtures thereof.

n) A human milk fortifier composition according to anyone of embodiments a) or g) to m) which is in the form of a powder to be reconstituted in human breast milk.

o). A human milk fortifier composition according to anyone of embodiment a) or g) to m) for use in fortifying human breast milk or fortified human breast milk.

p) Use of the human milk fortifier according to anyone of embodiments a) to o) to optimize the growth and development of an infant who was born prematurely, ELBW and/or VLBW.

q) A human milk fortifier composition according to anyone of embodiments a) to o) for use in supporting healthy growth at discharge from the hospital of infants who were born preterm, VLBW and/or ELBW.

r) A human milk fortifier composition according to anyone of embodiments a) to o) or q) for use in prevention and/or treatment of a condition selected in the group consisting of: sub-optimal growth and/or development, stunting of growth, infection, lung disease, developmental delays, blindness and/or bone metabolic disease.

s) A package comprising the human milk fortifier composition according to anyone of the embodiments a) to o) or q), wherein the package is a single-dosing device or a multi-dosing device.

All the embodiments as described in the above description shall be interpreted as illustrative and not in a limiting sense.

The invention claimed is:

1. A method for optimizing growth and development of an infant who was born prematurely, with extremely low birth weight (ELBW), and/or with very low birth weight (VLBW), the method comprising administering to the infant a composition comprising human breast milk and a human milk fortifier composition comprising:
   ingredients providing copper in an amount within at least one range selected from a group consisting of 13 to 42 µg, 5 to 30 µg/100 mL of the human breast milk, 1 to 30 µg/g of the human milk fortifier composition, 79 to 253 µg, or 26 to 84 µg;
   ingredients providing selenium in an amount within at least one range selected from a group consisting of 0.165 to 1.165 µg, 0.1 to 10 µg/100 mL of the human breast milk, 0.0025 to 25 µg/g of the human milk fortifier composition, 1 to 7 µg, 2 to 6 µg, or 0.33 to 2.33 µg;
   ingredients providing zinc in an amount within at least one range selected from a group consisting of 203 to 647 µg, 50 to 550 µg/100 mL of the human breast milk, 50 to 550 µg/g of the human milk fortifier composition, 1220 to 3880 µg, or 406 to 1293 µg;
   ingredients providing alpha-lactalbumin in an amount within at least one range selected from a group consisting of 0.06 to 0.22 g, 25 to 180 mg/100 mL of the human breast milk, 25 to 180 mg/g of the human milk fortifier composition, 0.4 to 1.31 g, or 0.13 to 0.44 g;
   ingredients providing casein in an amount within at least one range selected from a group consisting of 0.13 to 0.44 g, 10 to 500 mg/100 mL of the human breast milk, 10 to 500 mg/g of the human milk fortifier composition, 0.82 to 2.60 g, or 0.27 to 0.87 g;
   ingredients providing lactoferrin in an amount within at least one range selected from a group consisting of 0.08 to 0.27 g, 10 to 500 mg/100 mL of the human breast milk, 10 to 500 mg/g of the human milk fortifier composition, 0.50 to 1.58 g, or 0.17 to 0.53 g;
   ingredients providing alpha-tocopherol in an amount within at least one range selected from a group consisting of 0.40 to 1.27 mg, 5 to 1800 µg/100 mL of the human breast milk, 5 to 1800 µg/g of the human milk fortifier composition, 2.39 to 7.60 mg, or 0.80 to 2.53 mg;
   ingredients providing gamma-tocopherol in an amount within at least one range selected from a group consisting of 0.006 to 0.02 mg, 0.1 to 50 µg/100 mL of the human breast milk, 0.1 to 50 µg/g of the human milk fortifier composition, 0.04 to 0.13 mg, or 0.013 to 0.04 mg;
   ingredients providing nicotinic acid in an amount within at least one range selected from a group consisting of 0.40 to 1.29 µg, 0.5 to 18 µg/100 mL of the human breast milk, 0.5 to 18 µg/g of the human milk fortifier composition, 2.44 to 7.74 µg, or 0.81 to 2.58 µg;
   ingredients providing retinol in an amount within at least one range selected from a group consisting of 0.04 to 0.13 mg, 1 to 250 µg/100 mL of the human breast milk, 1 to 250 µg/g of the human milk fortifier composition, 0.24 to 0.75 mg, or 0.08 to 0.25 mg;
   ingredients providing difucosyllacto-N-Hexaose-a (DFSLTHN) in an amount within at least one range selected from a group consisting of 6 to 22 mg, 5 to 25 mg/100 mL of the human breast milk, 5 to 25 mg/g of the human milk fortifier composition, 40 to 128 mg, or 13 to 43 mg;
   ingredients providing monofucosyllacto-N-hexaose-III (FSLTNH3) in an amount within at least one range selected from a group consisting of 7 to 24 mg, 0.5 to 35 mg/100 mL of the human breast milk, 0.5 to 35 mg/g of the human milk fortifier composition, 45 to 145 mg, or 15 to 48 mg;
   ingredients providing 6'-galactosyllactose (GSLT6) in an amount within at least one range selected from a group consisting of 10 to 34 mg, 0.1 to 10 mg/100 mL of the human breast milk, 0.1 to 10 mg/g of the human milk fortifier composition, or 21 to 68 mg;
   ingredients providing lacto-N-neotetraose (LnNT) in an amount within at least one range selected from a group consisting of 7 to 26 mg, 0.1 to 25 mg/100 mL of the human breast milk, 0.1 to 25 mg/g of the human milk fortifier composition, 47 to 151 mg, or 15 to 51 mg;
   ingredients providing lacto-N-tetraose (LNT) in an amount within at least one range selected from a group consisting of 15 to 47 mg, 0.5 to 55 mg/100 mL of the human breast milk, 0.5 to 55 mg/g of the human milk fortifier composition, 87 to 279 mg, or 29 to 93 mg;
   ingredients providing 6'-sialyllactose (6'SL) in an amount within at least one range selected from a group consisting of 22 to 70 mg, 5 to 355 mg/100 mL of the human breast milk, 5 to 55 mg/g of the human milk fortifier composition, 132 to 421 mg, or 44 to 140 mg; and
   ingredients providing sialyllactose-N-tetraose-c (SLTNTC) in an amount within at least one range selected from a group consisting of 23 to 74 mg, 1 to 60 mg/100 mL of the human breast milk, 1 to 60 mg/g of the human milk fortifier composition, 139 to 443 mg, or 46 to 148 mg.

2. The method of claim 1, wherein the human milk fortifier composition comprises:
   the ingredients providing copper in an amount ranging from 13 to 42 µg;
   the ingredients providing selenium in an amount ranging from 0.165 to 1.165 µg;
   the ingredients providing zinc in an amount ranging from 203 to 647 µg;
   the ingredients providing alpha-lactalbumin in an amount ranging from 0.06 to 0.22 g;
   the ingredients providing caseins in an amount ranging from 0.13 to 0.44 g;
   the ingredients providing lactoferrin in an amount ranging from 0.08 to 0.27 g;
   the ingredients providing alpha-tocopherol in an amount ranging from 0.40 to 1.27 mg;
   the ingredients providing gamma-tocopherol in an amount ranging from 0.006 to 0.02 mg;

the ingredients providing nicotinic acid in an amount ranging from 0.40 to 1.29 μg;

the ingredients providing retinol in an amount ranging from 0.04 to 0.13 mg;

the ingredients providing DFSLTHN in an amount ranging from 6 to 22 mg;

the ingredients providing FSLTNH3 in an amount ranging from 7 to 24 mg;

the ingredients providing GSLT6 in an amount ranging from 10 to 34 mg;

the ingredients providing LnNT in an amount ranging from 7 to 26 mg;

the ingredients providing LNT in an amount ranging from 15 to 47 mg;

the ingredients providing 6' SL in an amount ranging from 22 to 70 mg; and the ingredients providing SLTNTC in an amount ranging from 23 to 74 mg.

3. The method of claim 1, wherein the human milk fortifier composition comprises:

ingredients providing copper in an amount ranging from 5 to 30 μg/100 mL of the human breast milk;

ingredients providing selenium in an amount ranging from 0.1 to 10 μg/100 mL of the human breast milk;

ingredients providing zinc in an amount ranging from 50 to 550 μg/100 mL of the human breast milk;

ingredients providing alpha-lactalbumin in an amount ranging from 25 to 180 mg/100 mL of the human breast milk;

ingredients providing casein in an amount ranging from 10 to 500 mg/100 mL of the human breast milk;

ingredients providing lactoferrin in an amount ranging from 10 to 500 mg/100 mL of the human breast milk;

ingredients providing alpha-tocopherol in an amount ranging from 5 to 1800 μg/100 mL of the human breast milk;

ingredients providing gamma-tocopherol in an amount ranging from 0.1 to 50 μg/100 mL of the human breast milk;

ingredients providing nicotinic acid in an amount ranging from 0.5 to 18 μg/100 mL of the human breast milk;

ingredients providing retinol in an amount ranging from 1 to 250 μg/100 mL of the human breast milk;

ingredients providing DFSLTHN in an amount ranging from 5 to 25 mg/100 mL of the human breast milk;

ingredients providing FSLTNH3 in an amount ranging from 0.5 to 35 mg/100 mL of the human breast milk;

ingredients providing GSLT6 in an amount ranging from 0.1 to 10 mg/100 mL of the human breast milk;

ingredients providing LnNT in an amount ranging from 0.1 to 25 mg/100 mL of the human breast milk;

ingredients providing LNT in an amount ranging from 0.5 to 55 mg/100 mL of the human breast milk;

ingredients providing 6' SL in an amount ranging from 5 to 355 mg/100 mL of the human breast milk; and ingredients providing SLTNTC in an amount ranging from 1 to 60 mg/100 mL of the human breast milk.

4. The method of claim 1, wherein the human milk fortifier composition comprises:

ingredients providing copper in an amount ranging from 1 to 30 μg/g of the human milk fortifier composition;

ingredients providing selenium in an amount ranging from 0.0025 to 25 μg/g of the human milk fortifier composition;

ingredients providing zinc in an amount ranging from 50 to 550 μg/g of the human milk fortifier composition;

ingredients providing alpha-lactalbumin in an amount ranging from 25 to 180 mg/g of the human milk fortifier composition;

ingredients providing caseins in an amount ranging from 10 to 500 mg/g of the human milk fortifier composition;

ingredients providing lactoferrin in an amount ranging from 10 to 500 mg/g of the human milk fortifier composition;

ingredients providing alpha-tocopherol in an amount ranging from 5 to 1800 μg/g of the human milk fortifier composition;

ingredients providing gamma-tocopherol in an amount ranging from 0.1 to 50 μg/g of the human milk fortifier composition;

ingredients providing nicotinic acid in an amount ranging from 0.5 to 18 μg/g of the human milk fortifier composition;

ingredients providing retinol in an amount ranging from 1 to 250 μg/g of the human milk fortifier composition;

ingredients providing DFSLTHN in an amount ranging from 5 to 25 mg/g of the human milk fortifier composition;

ingredients providing FSLTNH3 in an amount ranging from 0.5 to 35 mg/g of the human milk fortifier composition;

ingredients providing GSLT6 in an amount ranging from 0.1 to 10 mg/g of the human milk fortifier composition;

ingredients providing LnNT in an amount ranging from 0.1 to 25 mg/g of the human milk fortifier composition;

ingredients providing LNT in an amount ranging from 0.5 to 55 mg/g of the human milk fortifier composition;

ingredients providing 6' SL in an amount ranging from 5 to 55 mg/g of the human milk fortifier composition; and ingredients providing SLTNTC in an amount ranging from 1 to 60 mg/g of the human milk fortifier composition.

5. The method of claim 1, wherein the human milk fortifier composition comprises:

ingredients providing copper in an amount ranging from 79 to 253 μg;

ingredients providing selenium in an amount ranging from 1 to 7 μg or 2 to 6 μg;

ingredients providing zinc in an amount ranging from 1220 to 3880 μg;

ingredients providing alpha-lactalbumin in an amount ranging from 0.4 to 1.31 g;

ingredients providing caseins in an amount ranging from 0.82 to 2.60 g;

ingredients providing lactoferrin in an amount ranging from 0.50 to 1.58 g;

ingredients providing alpha-tocopherol in an amount ranging from 2.39 to 7.60 mg;

ingredients providing gamma-tocopherol in an amount ranging from 0.04 to 0.13 mg;

ingredients providing nicotinic acid in an amount ranging from 2.44 to 7.74 μg;

ingredients providing retinol in an amount ranging from 0.24 to 0.75 mg;

ingredients providing DFSLTHN in an amount ranging from 40 to 128 mg;

ingredients providing FSLTNH3 in an amount ranging from 45 to 145 mg;

ingredients providing GSLT6 in an amount ranging from 21 to 68 mg;

ingredients providing LnNT in an amount ranging from 47 to 151 mg;

ingredients providing LNT in an amount ranging from 87 to 279 mg;
ingredients providing 6'SL in an amount ranging from 132 to 421 mg; and
ingredients providing SLTNTC in an amount ranging from 139 to 443 mg.

6. The method of claim 1, wherein the human milk fortifier composition comprises:
ingredients providing copper in an amount ranging from 26 to 84 μg;
ingredients providing selenium in an amount ranging from 0.33 to 2.33 μg;
ingredients providing zinc in an amount ranging from 406 to 1293 μg;
ingredients providing alpha-lactalbumin in an amount ranging from 0.13 to 0.44;
ingredients providing caseins in an amount ranging from 0.27 to 0.87 g;
ingredients providing lactoferrin in an amount ranging from 0.17 to 0.53 g;
ingredients providing alpha-tocopherol in an amount ranging from 0.80 to 2.53 mg;
ingredients providing gamma-tocopherol in an amount ranging from 0.013 to 0.04 mg;
ingredients providing nicotinic acid in an amount ranging from 0.81 to 2.58 μg;
ingredients providing retinol in an amount ranging from 0.08 to 0.25 mg;
ingredients providing DFSLTHN in an amount ranging from 13 to 43 mg;
ingredients providing FSLTNH3 in an amount ranging from 15 to 48 mg;
ingredients providing GSLT6 in an amount ranging from 21 to 68 mg;
ingredients providing LnNT in an amount ranging from 15 to 51 mg;
ingredients providing LNT in an amount ranging from 29 to 93 mg;
ingredients providing 6'SL in an amount ranging from 44 to 140 mg; and
ingredients providing SLTNTC in an amount ranging from 46 to 148 mg.

7. The method of claim 1, wherein the composition is administered to the infant from between 36 and 50 weeks of age to 9 months of post-menstrual age or until the infant reaches a body weight of 8 kilograms.

\* \* \* \* \*